US00RE45435E

(19) United States
(12) Reissued Patent
Modak et al.

(10) Patent Number: US RE45,435 E
(45) Date of Reissued Patent: Mar. 24, 2015

(54) ZINC SALT COMPOSITIONS FOR THE PREVENTION OF DERMAL AND MUCOSAL IRRITATION

(71) Applicant: The Trustees of Columbia University in the City of New York, New York, NY (US)

(72) Inventors: Shanta M. Modak, River Edge, NJ (US); Milind S. Shintre, Karvenagar Pune (IN); Lauserpina Caraos, Hollis, NY (US); Trupti Gaonkar, Branchburg, NJ (US)

(73) Assignee: The Trustees of Columbia University in the City of New York, New York, NY (US)

(21) Appl. No.: 13/673,945

(22) Filed: Nov. 9, 2012

Related U.S. Patent Documents

Reissue of:
(64) Patent No.: 7,951,840
Issued: May 31, 2011
Appl. No.: 10/622,272
Filed: Jul. 17, 2003

U.S. Applications:
(63) Continuation-in-part of application No. PCT/US03/03896, filed on Feb. 7, 2003.

(60) Provisional application No. 60/355,549, filed on Feb. 7, 2002.

(51) Int. Cl.
*A61K 31/315* (2006.01)
*A61Q 19/00* (2006.01)
*A61K 8/27* (2006.01)

(52) U.S. Cl.
CPC .. *A61Q 19/00* (2013.01); *A61K 8/27* (2013.01)
USPC ..... 424/642; 514/494

(58) Field of Classification Search
CPC ..... A61K 8/27; A61K 8/365; A61K 8/416; A61Q 19/00
See application file for complete search history.

(56) References Cited

U.S. PATENT DOCUMENTS

| | | | | |
|---|---|---|---|---|
| 3,257,276 | A | 6/1966 | Broh-Kahn et al. | |
| 3,485,915 | A | 12/1969 | Gerstein et al. | 424/81 |
| 3,960,745 | A | 6/1976 | Billany et al. | |
| 4,243,657 | A | 1/1981 | Okumura et al. | |
| 4,318,907 | A | 3/1982 | Kligman et al. | |
| 4,393,076 | A | 7/1983 | Noda et al. | |
| 4,478,853 | A | 10/1984 | Chaussee | 424/358 |
| 4,587,266 | A | 5/1986 | Verdicchio | |
| 4,604,384 | A | 8/1986 | Smith et al. | |
| 4,814,334 | A | 3/1989 | Salkin | |
| 4,853,978 | A | 8/1989 | Stockum | 2/167 |
| 4,868,169 | A * | 9/1989 | O'Laughlin et al. | 514/179 |
| 4,870,108 | A | 9/1989 | Page | |
| 4,889,844 | A | 12/1989 | Silvetti, Sr. et al. | 514/60 |
| 4,910,205 | A | 3/1990 | Kogan et al. | |
| 4,919,837 | A | 4/1990 | Gluck | |
| 4,956,170 | A | 9/1990 | Lee | |
| 4,963,591 | A | 10/1990 | Fourman et al. | |
| 4,966,754 | A | 10/1990 | Purohit et al. | |
| 5,031,245 | A | 7/1991 | Milner | |
| 5,059,416 | A | 10/1991 | Cherukuri et al. | |
| 5,073,372 | A * | 12/1991 | Turner et al. | 424/401 |
| 5,089,205 | A | 2/1992 | Huang et al. | |
| 5,110,809 | A | 5/1992 | Wang et al. | |
| 5,116,602 | A | 5/1992 | Robinson et al. | |
| 5,133,090 | A | 7/1992 | Modak et al. | 2/168 |
| 5,147,648 | A | 9/1992 | Bannert | |
| 5,164,107 | A | 11/1992 | Khan et al. | |
| 5,208,031 | A | 5/1993 | Kelly | 424/412 |
| 5,357,636 | A | 10/1994 | Dresdner, Jr. et al. | 2/161.7 |

(Continued)

FOREIGN PATENT DOCUMENTS

| | | |
|---|---|---|
| DE | 4140474 | 6/1993 |
| DE | 19523320 | 1/1997 |
| EP | 0041448 | 12/1981 |
| EP | 304802 | 3/1989 |
| EP | 402078 | 9/1992 |
| EP | 0521455 | 1/1993 |
| EP | 0604848 | 7/1994 |
| EP | 0674896 | 10/1995 |
| EP | 0694310 | 1/1996 |
| EP | 0313302 | 4/1998 |

(Continued)

OTHER PUBLICATIONS

Cimiotti JP, Marmur ES, Nesin M, Hamlin-Cook P, Larson EL. Adverse reactions associated with an alcohol-based hand antiseptic among nurses in a neonatal intensive care unit. *Am. J. Infect. Control* 2003:131:43-48.

Bleasel N, Tate B, Rademaker M. Allergic contact dermatitis following exposure to essential oils. *Australian Journal of Dermatology* 2002;43:211-213.

Vikaplana J. Romaguera C. Contact dermatitis from the essential oil of tangerine in fragrances. *Contact Dermatitis* 2002;46:108.

(Continued)

*Primary Examiner* — James D Anderson
(74) *Attorney, Agent, or Firm* — Baker Botts, L.L.P.

(57) ABSTRACT

The addition of low concentrations of combinations of water-soluble organic salts of zinc to gels, creams, lotions or ointments can increase the ability of these products to reduce or prevent exogenous irritants from causing irritation of the underlying substrate. The addition of low concentrations of combinations of water-soluble organic zinc salts to these gels, creams, lotions or ointments also can reduce the irritation of skin or mucous membranes caused by the addition of potentially-irritating substances such as spermicides, microbicides, fungicides or other therapeutic agents to the gel, cream, lotion or ointment. The advantages of this anti-irritant approach over others, which generally employ high concentrations of single zinc salts, are the reduced potential for zinc toxicity, the reduced potential for toxicity related to zinc itself, and the preservation of the desirable biological properties of potentially-irritating therapeutic substances added to the gel, cream, lotion or ointment.

15 Claims, No Drawings

(56) References Cited

U.S. PATENT DOCUMENTS

| | | | | |
|---|---|---|---|---|
| 5,403,864 | A | 4/1995 | Bruch et al. | 514/721 |
| 5,447,930 | A | 9/1995 | Nayak | |
| 5,516,510 | A | 5/1996 | Beilfuss et al. | 424/65 |
| 5,591,442 | A | 1/1997 | Diehl et al. | 424/401 |
| 5,599,549 | A | 2/1997 | Wivell et al. | |
| 5,612,324 | A | 3/1997 | Guang Lin et al. | |
| 5,624,675 | A | 4/1997 | Kelly | |
| 5,624,962 | A | 4/1997 | Takeuchi et al. | |
| 5,648,389 | A | 7/1997 | Gans et al. | |
| 5,658,575 | A | 8/1997 | Ribier et al. | |
| 5,705,532 | A | 1/1998 | Modak et al. | 514/635 |
| 5,708,023 | A | 1/1998 | Modak et al. | 514/494 |
| 5,736,574 | A | 4/1998 | Burnier et al. | |
| 5,750,122 | A | 5/1998 | Evans et al. | |
| 5,753,270 | A | 5/1998 | Beauchamp et al. | |
| 5,763,412 | A | 6/1998 | Khan et al. | |
| 5,776,430 | A | 7/1998 | Osborne et al. | |
| 5,804,203 | A | 9/1998 | Hahn et al. | |
| 5,830,488 | A | 11/1998 | Suzuki et al. | |
| 5,885,562 | A | 3/1999 | Lowry et al. | |
| 5,902,572 | A * | 5/1999 | Luebbe et al. | 424/66 |
| 5,906,808 | A | 5/1999 | Osborne et al. | |
| 5,951,993 | A | 9/1999 | Scholz et al. | 424/405 |
| 5,965,137 | A | 10/1999 | Petrus | |
| 5,965,310 | A | 10/1999 | Yamana | |
| 5,965,610 | A | 10/1999 | Modak et al. | 514/494 |
| 5,980,477 | A | 11/1999 | Kelly | 602/77 |
| 5,980,925 | A | 11/1999 | Jampani et al. | |
| 5,985,918 | A | 11/1999 | Modak et al. | 514/494 |
| 5,985,931 | A | 11/1999 | Modak et al. | |
| 6,022,551 | A | 2/2000 | Jampani et al. | 424/405 |
| 6,037,386 | A | 3/2000 | Modak et al. | 524/105 |
| 6,040,347 | A | 3/2000 | Cupferman et al. | |
| 6,045,817 | A | 4/2000 | Ananthapadmanabhan et al. | |
| 6,107,261 | A | 8/2000 | Taylor et al. | |
| 6,110,908 | A | 8/2000 | Guthery | |
| 6,136,771 | A | 10/2000 | Taylor et al. | |
| 6,183,766 | B1 * | 2/2001 | Sine et al. | 424/405 |
| 6,187,327 | B1 | 2/2001 | Stack | |
| 6,204,230 | B1 | 3/2001 | Taylor et al. | |
| 6,211,243 | B1 | 4/2001 | Johnson | |
| 6,224,579 | B1 | 5/2001 | Modak | |
| 6,248,343 | B1 | 6/2001 | Jampani et al. | |
| 6,287,577 | B1 | 9/2001 | Beerse et al. | |
| 6,287,583 | B1 | 9/2001 | Warren | |
| 6,294,186 | B1 | 9/2001 | Beerse et al. | |
| 6,319,958 | B1 | 11/2001 | Johnson et al. | |
| 6,321,750 | B1 | 11/2001 | Kelly | 128/844 |
| 6,323,171 | B1 | 11/2001 | Fonsny et al. | |
| 6,344,218 | B1 * | 2/2002 | Dodd et al. | 424/605 |
| 6,352,701 | B1 | 3/2002 | Scholz et al. | 424/405 |
| 6,376,522 | B1 | 4/2002 | Holzl et al. | |
| 6,387,357 | B1 | 5/2002 | Chopra et al. | |
| 6,403,067 | B1 | 6/2002 | Schamper et al. | |
| 6,403,071 | B1 | 6/2002 | Scavone et al. | |
| 6,414,032 | B1 | 7/2002 | Johnson | |
| 6,420,431 | B1 | 7/2002 | Johnson | |
| 6,426,062 | B1 | 7/2002 | Chopra et al. | |
| 6,485,716 | B1 | 11/2002 | Fei et al. | |
| 6,511,657 | B2 | 1/2003 | Avendano et al. | |
| 6,582,711 | B1 | 6/2003 | Asmus et al. | |
| 6,582,719 | B2 | 6/2003 | Modak | |
| 6,613,312 | B2 | 9/2003 | Rizvi et al. | |
| 6,682,749 | B1 | 1/2004 | Potechin et al. | |
| 6,723,689 | B1 | 4/2004 | Hoang et al. | 510/130 |
| 6,843,784 | B2 | 1/2005 | Modak | |
| 6,846,846 | B2 | 1/2005 | Modak | |
| 7,329,412 | B2 | 2/2008 | Modak | |
| 7,435,429 | B2 | 10/2008 | Modak | |
| 7,537,779 | B2 | 5/2009 | Modak | |
| 7,563,461 | B2 | 7/2009 | Modak | |
| 7,745,425 | B2 * | 6/2010 | Modak et al. | 514/159 |
| 2002/0022660 | A1 | 2/2002 | Jampani et al. | |
| 2002/0098159 | A1 * | 7/2002 | Wei et al. | 424/70.1 |
| 2002/0165130 | A1 | 11/2002 | Johnson et al. | |
| 2003/0134780 | A1 | 7/2003 | Patt | |
| 2003/0152644 | A1 * | 8/2003 | Modak et al. | 424/667 |
| 2003/0157138 | A1 | 8/2003 | Eini et al. | |
| 2003/0211066 | A1 | 11/2003 | Scholz | |
| 2004/0102429 | A1 | 5/2004 | Modak et al. | |
| 2004/0208908 | A1 | 10/2004 | Modak | |
| 2004/0219227 | A1 | 11/2004 | Modak | |
| 2004/0247685 | A1 | 12/2004 | Modak | |
| 2004/0253275 | A1 | 12/2004 | Eini et al. | |
| 2005/0019431 | A1 | 1/2005 | Modak et al. | |
| 2005/0048139 | A1 | 3/2005 | Modak | |
| 2005/0124725 | A1 | 6/2005 | Modak | |
| 2005/0192547 | A1 | 9/2005 | Modak | |
| 2005/0238602 | A1 | 10/2005 | Modak et al. | |
| 2005/0281762 | A1 | 12/2005 | Modak et al. | |
| 2006/0099237 | A1 | 5/2006 | Modak | |
| 2006/0141017 | A1 | 6/2006 | Kling et al. | |
| 2007/0020342 | A1 | 1/2007 | Modak | |
| 2008/0075761 | A1 | 3/2008 | Modak | |
| 2008/0311231 | A1 | 12/2008 | Modak | |
| 2009/0004122 | A1 | 1/2009 | Modak | |
| 2009/0029961 | A1 | 1/2009 | Modak | |
| 2009/0035228 | A1 | 2/2009 | Modak | |
| 2009/0035390 | A1 | 2/2009 | Modak | |
| 2009/0175806 | A1 | 7/2009 | Modak | |

FOREIGN PATENT DOCUMENTS

| | | |
|---|---|---|
| EP | 1001012 | 5/2000 |
| FR | 2729050 | 7/1996 |
| JP | 10328284 | 12/1998 |
| RU | 2166309 | 5/2001 |
| SU | 833240 | 5/1981 |
| WO | WO8400111 | 1/1984 |
| WO | WO8704350 | 7/1987 |
| WO | WO8800795 | 2/1988 |
| WO | WO8803799 | 6/1988 |
| WO | WO8905645 | 6/1989 |
| WO | WO9307903 | 4/1993 |
| WO | WO9318745 | 9/1993 |
| WO | WO9318852 | 9/1993 |
| WO | WO9415461 | 7/1994 |
| WO | WO 94/18939 | 9/1994 |
| WO | WO9526134 | 10/1995 |
| WO | WO9824426 | 6/1998 |
| WO | WO9851275 | 11/1998 |
| WO | WO9903463 | 1/1999 |
| WO | WO99/38505 | 5/1999 |
| WO | WO9938505 | 8/1999 |
| WO | WO 99/51192 | 10/1999 |
| WO | WO9960852 | 12/1999 |
| WO | WO9963816 | 12/1999 |
| WO | WO0037042 | 6/2000 |
| WO | WO0141573 | 6/2001 |
| WO | 03034994 | 5/2003 |
| WO | 03003896 | 8/2003 |
| WO | WO 03/066001 A2 | 8/2003 |
| WO | WO03066001 | 8/2003 |
| WO | WO03083028 | 10/2003 |
| WO | WO 2004/014416 | 2/2004 |
| WO | WO 2006/099359 | 9/2006 |
| WO | WO2007/069214 | 6/2007 |
| WO | WO 2007/069214 | 9/2007 |

OTHER PUBLICATIONS

Nair B. Final report on the safety assessment of Menta Piperita (Peppermint) oil, Mentha Piperita (Peppermint) Leaf extract, Mentha Piperita (Peppermint) leaf and Mentha Piperita (Peppermint) water. *International Journal of Taxicology* 2001;20(Suppl 3):61-73.

Larsen W. Nakayama H, Fischer T, Elsner P, Frosch P, Burrows D. Jordan W, Shaw S, Wilkinson J, Marks J Jr, Sugawara M, Nethercott M, Nethercott J. Fragrance contact dermatitis: a worldwide multicenter investigation (Part (II). *Contact Dermatitis* 2001;44:344-346.

(56) References Cited

OTHER PUBLICATIONS

Wohrl S, Hemmer W, Focke M, Gotz M, Jarisch R. The significance of fragrance mix, balsam of Peru, colophony and propolis as screening tools in the detection of fragrance allergy. *British Journal of Dermatology* 2001;145(2):268-273.
Sugiura M, Hayakawa R, Kato Y, Sugiura K, Hashimoto R. Results of patch testing with lavender oils in Japan. *Contact Dermatitis* 2000;43:157-160.
Modak et al., 2005, A topical cream containing a zinc gel (allergy guard) as a prophylactic against latex glove-related contact dermatitis. Dermatitis. 16(1):22-7.
Modak S.M, et al., A Topical Zinc Gluconate Gel Composition for the Prevention of latex/Starch Glove Related Allergic Reactions: Pilot Study in Volunteers. In: Programs and Abstracts of the 37$^{th}$ Interscience Conference on Antimiocrobial Agents and Chemotherapy, Toronto: 1997; American Society for Microbiology Washington DC. Abstract J-52.
Goodman and Gilman's The Pharmacological Basis of Therapeutics (Goodman Gilman A, Rall TW, Nies AS, Taylor P, ed. (Pergamon Press; Elmsford, N.Y.: 1990).
Bush et al., 1986, "Pig skin as test substrate for evaluating topical antimicrobial activity" J Clin Microbiol 24:343-348.
Meyer et al., 1978, "The skin of domestic mammals as a model for the human skin, with special reference to the domestic pig." Curr. Problem Dermatol 7:39-52.
Rosenthal, S.L.; Effect of Medicaments on the Motility of the Oral Flora with Special Reference to the Treatment of Vincent's Infection; II. Journal of Dental Research; 1943; vol. 22, pp. 491-494.
Lansdown, "Interspecies variations in response to topical application of selected zinc compounds," Food Chem Toxicol. Jan. 1991;29(1):57-64.
U.S. Appl. No. 12/444,089, Modak.
U.S. Appl. No. 10/600,257.
U.S. Appl. No. 10/633,204: Apr. 4, 2005 Non-Final Office Action.
U.S. Appl. No. 10/633,204: Oct. 7, 2005 Response to Non-Final Office Action.
U.S. Appl. No. 10/633,204: Nov. 25, 2005 Response to Non-Final Office Action.
U.S. Appl. No. 10/633,204: Mar. 22, 2006 Response to Non-Final Office Action.
U.S. Appl. No. 10/633,204: Jun. 7, 2006 Non-Final Office Action.
U.S. Appl. No. 10/633,204: Nov. 7, 2006 Response to Non-Final Office Action.
U.S. Appl. No. 10/633,204: Jun. 2, 2008 Final Office Action.
U.S. Appl. No. 10/633,204: Aug. 28, 2008 Response to Final Office Action.
U.S. Appl. No. 10/633,204: Oct. 8, 2008 Non-Final Office Action.
U.S. Appl. No. 10/633,204: Jan. 8, 2009 Response to Non-Final Office Action.
U.S. Appl. No. 10/633,204: Apr. 17, 2009 Final Office Action.
U.S. Appl. No. 10/785,207: Nov. 19, 2007 Non-Final Office Action.
U.S. Appl. No. 10/785,207: Feb. 19, 2008 Response to Non-Final Office Action.
U.S. Appl. No. 10/785,207: May 14, 2008 Final Office Action.
U.S. Appl. No. 10/785,207: Aug. 13, 2008 Response to Final Office Action.
U.S. Appl. No. 10/785,207: Sep. 22, 2008 Non-Final Office Action.
U.S. Appl. No. 10/785,207: Dec. 18, 2008 Response to Non-Final Office Action.
U.S. Appl. No. 10/785,207: Mar. 5, 2009 Final Office Action.
U.S. Appl. No. 10/785,207: May 28, 2009 Response to Final Office Action.
U.S. Appl. No. 10/785,207: Aug. 11, 2009 Non-Final Office Action.
U.S. Appl. No. 10/786,681: May 21, 2007 Non-Final Office Action.
U.S. Appl. No. 10/786,681: Sep. 6, 2007 Response to Non-Final Office Action.
U.S. Appl. No. 10/786,681: Nov. 21, 2007 Final Office Action.
U.S. Appl. No. 10/786,681: Feb. 21, 2008 Response to Final Office Action.
U.S. Appl. No. 10/786,681: Jul. 7, 2008 Non-Final Office Action.
U.S. Appl. No. 10/786,681: Oct. 2, 2008 Response to Non-Final Office Action.
U.S. Appl. No. 10/786,681: Dec. 23, 2008 Final Office Action.
U.S. Appl. No. 10/786,681: Mar. 23, 2009 Response to Final Office Action.
U.S. Appl. No. 10/786,681: May 27, 2009 Non-Final Office Action.
U.S. Appl. No. 10/891,624: Apr. 10, 2007 Non-Final Office Action.
U.S. Appl. No. 10/891,624: Oct. 3, 2007 Response to Non-Final Office Action.
U.S. Appl. No. 10/891,624: Dec. 18, 2007 Final Office Action.
U.S. Appl. No. 10/891,624: Apr. 7, 2008 Response to Final Office Action.
U.S. Appl. No. 10/891,624: Jul. 24, 2008 Non-Final Office Action.
U.S. Appl. No. 10/891,624: Oct. 22, 2008 Response to Non-Final Office Action.
U.S. Appl. No. 10/891,624: Jan. 26, 2009 Final Office Action.
U.S. Appl. No. 10/891,624: Apr. 23, 2009 Response to Final Office Action.
U.S. Appl. No. 10/891,624: Aug. 6, 2009 Non-Final Office Action.
U.S. Appl. No. 10/892,034: Jan. 29, 2008 Non-Final Office Action.
U.S. Appl. No. 10/892,034: Jun. 17, 2008 Response to Non-Final Office Action.
U.S. Appl. No. 10/892,034: Aug. 27, 2008 Final Office Action.
U.S. Appl. No. 10/892,034: Jan. 27, 2009 Response to Final Office Action.
U.S. Appl. No. 10/892,034: Apr. 8, 2009 Non-Final Office Action.
U.S. Appl. No. 10/892,034: Jul. 2, 2009 Response to Non-Final Office Action.
U.S. Appl. No. 11/327,677: Jun. 1, 2009 Non-Final Office Action.
U.S. Appl. No. 11/250,241: Jun. 12, 2009 Non-Final Office Action.
U.S. Appl. No. 11/143,012: Oct. 31, 2008 Non-Final Office Action.
U.S. Appl. No. 11/143,012: Jan. 16, 2009 Response to Non-Final Office Action.
U.S. Appl. No. 11/143,012: Mar. 24, 2009 Notice of Allowance.
U.S. Appl. No. 11/031,258: Jun. 6, 2007 Non-Final Office Action.
U.S. Appl. No. 11/031,258: Aug. 22, 2007 Response to Non-Final Office Action.
U.S. Appl. No. 11/031,258: Dec. 6, 2007 Notice of Allowance.
U.S. Appl. No. 10/047,631: Nov. 14, 2003 Non-Final Office Action.
U.S. Appl. No. 10/047,631: Apr. 16, 2004 Response to Non-Final Office Action.
U.S. Appl. No. 10/047,631: Jul. 12, 2004 Notice of Allowance.
U.S. Appl. No. 09/746,670: Jan. 10, 2003 Non-Final Office Action.
U.S. Appl. No. 09/746,670: Jul. 9, 2003 Response to Non-Final Office Action.
U.S. Appl. No. 09/746,670: Sep. 24, 2003 Final Office Action.
U.S. Appl. No. 09/746,670: Dec. 29, 2003 Response to Final Office Action.
U.S. Appl. No. 09/746,670: Feb. 13, 2004 Non-Final Office Action.
U.S. Appl. No. 09/746,670: Aug. 11, 2004 Response to Non-Final Office Action.
U.S. Appl. No. 09/746,670: Dec. 14, 2004 Notice of Allowance.
U.S. Appl. No. 09/746,670: Mar. 14, 2005 Request for Continued Examination.
U.S. Appl. No. 09/746,670: Jun. 17, 2005 Non-Final Office Action.
U.S. Appl. No. 09/746,670: Aug. 19, 2005 Response to Non-Final Office Action.
U.S. Appl. No. 09/746,670: Nov. 7, 2005 Notice of Allowance.
U.S. Appl. No. 09/746,670: Jan. 26, 2006 Request for Continued Examination.
U.S. Appl. No. 09/746,670: Oct. 2, 2006 Non-Final Office Action.
U.S. Appl. No. 09/746,670: Jan. 3, 2007 Response to Non-Final Office Action.
U.S. Appl. No. 09/746,670: Mar. 13, 2007 Final Office Action.
U.S. Appl. No. 09/746,670: May 14, 2007 Response to Final Office Action.
U.S. Appl. No. 09/746,670: Sep. 4, 2007 Notice of Allowance.
U.S. Appl. No. 10/600,257: Dec. 21, 2004 Non-Final Office Action.
U.S. Appl. No. 10/600,257: Mar. 24, 2005 Response to Non-Final Office Action.
U.S. Appl. No. 10/600,257: Jun. 7, 2005 Notice of Allowance.
U.S. Appl. No. 10/600,257: Sep. 9, 2005 Request for Continued Examination.

(56) References Cited

OTHER PUBLICATIONS

U.S. Appl. No. 10/600,257: Sep. 27, 2005 Non-Final Office Action.
U.S. Appl. No. 10/600,257: Nov. 28, 2005 Response to Non-Final Office Action.
U.S. Appl. No. 10/600,257: Jun. 4, 2008 Notice of Allowance.
U.S. Appl. No. 10/600,257: Apr. 17, 2009 Notice of Allowance.
U.S. Appl. No. 09/775,775: Dec. 3, 2002 Notice of Allowance.
U.S. Appl. No. 10/674,592: Nov. 15, 2004 Notice of Abandonment.
U.S. Appl. No. 09/281,872: Jul. 3, 2000 Non-Final Office Action.
U.S. Appl. No. 09/281,872: Oct. 6, 2000 Response to Non-Final Office Action.
U.S. Appl. No. 09/281,872: Oct. 26, 2000 Notice of Allowance.
U.S. Appl. No. 09/777,121: Feb. 24, 2003 Non-Final Office Action.
U.S. Appl. No. 09/777,121: Aug. 26, 2003 Response to Non-Final Office Action.
U.S. Appl. No. 09/777,121: Oct. 6, 2003 Notice of Non-Compliant Amendment.
U.S. Appl. No. 09/777,121: Dec. 10, 2003 Response to Non-Final Office Action.
U.S. Appl. No. 09/777,121: Jan. 30, 2004 Final Office Action.
U.S. Appl. No. 09/777,121: Jul. 2, 2004 Response to Final Office Action.
U.S. Appl. No. 09/777,121: Aug. 2, 2004 Advisory Action.
U.S. Appl. No. 09/777,121: Aug. 11, 2004 Notice of Abandonment.
U.S. Appl. No. 09/777,121: Aug. 23, 2004 Request for Continued Examination/Petition to Revive.
U.S. Appl. No. 09/777,121: Sep. 24, 2004 Notice of Allowance.
U.S. Appl. No. 10/414,902: Feb. 10, 2006 Notice of Abandonment.
U.S. Appl. No. 11/446,347, filed Jun. 2, 2006.
U.S. Appl. No. 10/892,034, filed Jul. 15, 2004.
U.S. Appl. No. 11/327,677, filed Jan. 6, 2006.
U.S. Appl. No. 10/891,624, filed Jul. 15, 2004.
U.S. Appl. No. 08/492,080, filed Jun. 28, 1995.
U.S. Appl. No. 08/860,054, filed Dec. 4, 1996.
U.S. Appl. No. 08/871,071, filed Jun. 9, 1997.
U.S. Appl. No. 09/387,550, filed Aug. 31, 1999.
U.S. Appl. No. 10/785,207, filed Feb. 24, 2004.
U.S. Appl. No. 10/786,681, filed Feb. 25, 2004.
U.S. Appl. No. 08/218,666, filed Mar. 28, 1994.
U.S. Appl. No. 11/446,347, Sep. 1, 2009 Non-Final Office Action.
U.S. Appl. No. 10/892,034, Oct. 9, 2009 Final Office Action.
U.S. Appl. No. 11/327,677, Aug. 27, 2009 Response to Non-Final Office Action.
U.S. Appl. No. 11/327,677, Nov. 2, 2009 Notice of Allowance.
U.S. Appl. No. 10/891,624, Nov. 4, 2009 Response to Non-final Office Action.
U.S. Appl. No. 10/785,207, Nov. 2, 2009 Response to Non-Final Office Action.
U.S. Appl. No. 10/786,681, Aug. 27, 2009 Response to Non-Final Office Action.
U.S. Appl. No. 10/786,681, Nov. 24, 2009 Final Office Action.
U.S. Appl. No. 08/492,080, Sep. 13, 1996 Non-Final Office Action.
U.S. Appl. No. 08/492,080, Jan. 13, 1997 Response to Non-Final Office Action.
U.S. Appl. No. 08/492,080, Apr. 19, 1997 Final Office Action.
U.S. Appl. No. 08/492,080, Jul. 9, 1997 Response to Final Office Action.
U.S. Appl. No. 08/492,080, Aug. 5, 1997 Examiner Interview Summary Record.
U.S. Appl. No. 08/492,080, Aug. 6, 1997 Notice of Allowance.
U.S. Appl. No. 08/760,054, Mar. 28, 1997 Non-Final Office Action.
U.S. Appl. No. 08/760,054, Jul. 28, 1997 Response to Non-Final Office Action.
U.S. Appl. No. 08/760,054, Nov. 19, 1997 Final Office Action.
U.S. Appl. No. 08/760,054, Apr. 17, 1998 Notice of Appeal Filed.
U.S. Appl. No. 08/760,054, Apr. 17, 1998 Amendment/Argument after Notice of Appeal.
U.S. Appl. No. 08/760,054, May 15, 1998 Advisory Action.
U.S. Appl. No. 08/760,054, Aug. 17, 1998 Express Abandonment.
U.S. Appl. No. 08/760,054, Aug. 17, 1998 Continuing Prosecution Application—Continuation (ACPA).
U.S. Appl. No. 08/760,054, Nov. 24, 1998 Non-Final Office Action.
U.S. Appl. No. 08/760,054, Mar. 17, 1999 Response to Non-Final Office Action.
U.S. Appl. No. 08/760,054, Jun. 18, 1999 Examiner's Amendment.
U.S. Appl. No. 08/760,054, Jun. 21, 1999 Notice of Allowance.
U.S. Appl. No. 08/871,071, May 8, 1998 Non-Final Office Action.
U.S. Appl. No. 08/871,071, Nov. 9, 1998 Response to Non-Final Office Action.
U.S. Appl. No. 08/871,071, Dec. 9, 1998 Terminal Disclaimer Approved.
U.S. Appl. No. 08/871,071, Dec. 16, 1998 Non-Final Office Action.
U.S. Appl. No. 08/871,071, Mar. 19, 1999 Response to Non-Final Office Action.
U.S. Appl. No. 08/871,071, Apr. 16, 1999 Notice of Allowance.
U.S. Appl. No. 09/387,550, Nov. 9, 1999 Notice of Allowance.
U.S. Appl. No. 09/387,550, Nov. 4, 2005 Certificate of Correction.
U.S. Appl. No. 09/387,550, Nov. 22, 2005 Certificate of Correction.
U.S. Appl. No. 08/218,666, Mar. 3, 1995 Non-Final Office Action.
U.S. Appl. No. 08/218,666, Sep. 7, 1995 Response to Non-Final Office Action.
U.S. Appl. No. 08/218,666, Dec. 18, 1995 Final Office Action.
3M Avagard Surgical and Healthcare Personnel Hand Antiseptic with Moisturizers news release, 3M Company, Jun. 11, 2001.
3M Avagard Surgical and Healthcare Personnel Hand Antiseptic with Moisturizers product description, 3M Company, 2001.
A-Z of exhibitors; at Central European Coatings Show, PPC1. Polymers Paint Colour Journal, No. 4433, vol. 190, p. 42, Oct. 1, 2000.
Beilfuss, "A multifunctional ingredient for deodorants," SOFW Journal, 1998, vol. 124, p. 360, 362-364, 366.
Bezic et al., 2003, "Composition and antimicrobial activity of *Achillea clavennae* L. essential oi." Phytother. Res. 17(9): 1037-1040.
Brehm-Stecher et ai. 2003, "Sensitization of *Staphylococcus aureus* and *Escherichi coli* to antibiotics by the sesquiterpenoids nerolidol, farnesol, bisabolol, and apritone." Antimicrobial Agents and Chemotherapy, 47(10):3357-3360.
de Abreu Gonzaga et al., "Composition and antibacterial activity of the essential oils from *Zanthoxylum rhoifolium."* 2003. Plant Med. 69(8):773-775.
De Groot A, Frosch PJ "Adverse reactions to fragrances: a clinical review." Contact Dermatitis 1997;36:57-86.
"Drug Information for the Health Care Professional," vol. 1A, USP-D1, 1989, Ninth Edition, pp. 792-793, Banta Company, VIR. s.
Fitzgerald, K.A., Davies, A., and Russel, A.D., "Mechanism of Action of Chlorhexidine Diacitate and Phenoxyethanol Singly and in Combination Against Gram-negative Bacteria," 215 Mibrobio 70:215-229 (1992).
"Fraicheur de Peau Fresh Skin Body Mist," International Product Alert, No. 9, vol. 14, May 5, 1997.
Garcia et al., 2003, "Virucidal activity of essential oils from aromatic plants of San Luis, Argentina." Phytother. Res. 17(9):1073-1075.
Goren et al., 2003, "Analysis of essential oil of *Coridothymus capitatus* (L.) and its antibacterial and antifungal activity." Z. Naturforsch. 58(9-10):687-690.
Hajhashemi et al., 2003, "Anti-inflammatory and analgesic properties of the leaf extracts and essential oil of *Lavandula angustifolia* Mill." Ethnopharmacol. 89(1 ):67-71.
Happi, Household & Personal Products Industry: New ingredients galore at SCC supplier's day, Chemical Business Newsbase, Aug. 1, 2000.
Heard, D.D., and Ashworth, R.W., "The Colloidal Properties of Chlorhexidine and its Interaction with Some Macromolecules," J. Pharm. Pharmac. 20:505-12, 1968.
Lawless, Julia. The Illustrated Encyclopedia of Essential Oils: The Complete Guide to the Use of Oils in Aromatherapy and Herbalism. Element Books, 1995, USA. pp. 132,162-164,169,223,227 and 228.
Lawrence, J.C. et al., "Evaluation of Phenoxeotol—Chlorhexidine Cream as a Prophylactic Antibacterial Agent in Burns," The Lancet, pp. 1037-1040, May 8, 1992.
Manufacturing Chemist: Japan approve Schulke & Mayr's Sensiva SC 50, Chemical Business Newsbase, Jul. 14, 2000.

(56) References Cited

OTHER PUBLICATIONS

Minami et al., 2003, "The inhibitory effect of essential oils on herpes simplex virus type-1 replication in vitro." Microbial Immunol. 47(1):681-684.
Modak S. et al., "Rapid Inactivation of Infections Pathogess by Chlorhexidine Coated Gloves," Infection Control and Hospital Epidemiology, 13:463-171, (1992).
Modak SM, et al., "A Topical Zinc Gluconate Gel Composition for the Prevention of latex/Starch Glove Related Allergic Reactions: Pilot Study in Volunteers." In: Programs and Abstracts of the 37th Interscience Conference on Antimicrobial Agents and Chemotherapy, Toronto: 1997; American Society for Microbiology Washington DC. Abstract J-52.
Molnycke Healthcare "Hibiclens Antiseptic/Antimicrobial Skin Cleanser" Nov. 10, 2006.
Paranagama et al., 2003, "Fungicidal and anti-aflatoxigenic effects of the essential oil of *Cymbopogon citratus* (DC.) Stapf. (lemongrass) against *Aspergillus flavus* Linle isolated from stored rice." Lett. Appi. Microbiol. 37(1):86-90.
Parfums, Cosmetiques, Aromes: Japan approves sale of new cosmetics ingredient, Chemical Business Newsbase, Jan. 16, 2001.
Physicians Desk Reference—39th Edition, 1985, p. 1858, Lotrisone.
Physicians Desk Reference—39th Edition, 1985, pp. 2037-2038, chlorhexidine.
Physicians Desk Reference—40th Edition, 1986, pp. 1781-1782, chlorhexidine.
Pfizer "Purell Instant Hand Sanitzer, Product Description" Nov. 10, 2006.
Prevacare:Antimicrobial Hand Gel product description, Johnson & Johnson, Advanced Wound Care, 2001.
Prevcare: Total solution skin care spray product description, Johnson & Johnson, Advanced Wound Care, 2001.
Robinson, K. "Heat beating technology; deodorant market," Soap Perfumery and Cosmetics, v. 69 No. 7 p. 34, Jul. 1996.
Rubbo et al., A Review of Sterilization and Disinfection, Year Book Medical Publishers, Chicago, 161-162 (1965).
S &M in Japan—Schulke & Mayr's Sensiva SC 50 deodorant active ingredient received approval for use in the Japanese market, SPC Asia No. 21, p. 35, May 2000.
Schmolka, I.R., "The Synergistic Effects of Nonionic Surfactants Upon Cationic Germicidal Agents," J. Soc. Cosmet. Chem., 24:577-592, 1973.
Schuhmacher et al., 2003, "Virucidal effect of peppermint oil on the enveloped viruses herpes simplex virus type 1 and type 2 in vitro." Phytomedicine 10:504-510.
Schwarzkopf: Moving into a new era , Euroepan Cosmetic Markets, Sep. 1, 1996.
Schwarzkopf cares, European Cosmetic Markets, No. 5, vol. 13, May 1, 1996.
Sensive SC 50 product description from manufacturer website (www.schuelkemayr.com), Schulke & Mayr, manufacturer, printed Apr. 4, 2001.
Shin, 2003, "Anti-*Aspergillus* activities of plant essential oils and their combination effects with ketoconazole or amphotericin B." Arch. Pharm. Res. 26(5):389-393.
Silva et al., 2003, "Analgesic and anti-inflammatory effects of essential oils of Eucalyptus." Ethnopharmacoi. 89(2-3);277-283.
SPC, Soap Perfumery and Cosmetics: New for deodorants: Sensiva SC 50, Chemical Business Newsbase, Aug. 12, 1999.
Valero and Salmera, 2003, "Antibacterial activity of 11 essential oils against *Bacillus cereus* in tyndallized carrot broth." Int. Food Microbiol. 85(1-2): 73-81.
Velluti et al., 2003, "Inhibitory effect of cinnamon, clove, lemongrass, oregano and palmarose essential oils on growth and fumonisin B1 production by *Fusarium proliferatum* in maize grain." Int. Food Microbiol. 89: 145-154.
Vichy launches oil-free mositurizer. Chemist & Druggist, p. 792, Jun. 8, 1996.
Woodruff, I. "Mixed feelings," Soap Perfumery & Cosmetics, No. 9, vol. 73, p. 39, Sep. 1, 2000.
Aiko Tanaka et al. "Effect of Various Types of Disinfectants on Skin Physiological Function." J. Nursing Science. Toyama Medical and Pharmaceutical University. 1999, vol. 2 pp. 49-58.
U.S. Appl. No. 12/715,026, filed Mar. 1, 2010.
U.S. Appl. No. 10/785,207, Jan. 29, 2010 Supplemental Response to Office Action.
U.S. Appl. No. 10/785,207, May 13, 2010 Final Office Action.
U.S. Appl. No. 10/786,681, Feb. 24, 2010 Response to Final Office Action.
U.S. Appl. No. 10/786,681, Mar. 30, 2010 Non-Final Office Action.
U.S. Appl. No. 10/892,034, Feb. 8, 2010 Response to Final Office Action.
U.S. Appl. No. 10/892,034, May 17, 2010 Non-Final Office Action.
U.S. Appl. No. 11/327,677, Feb. 23, 2010 Notice of Allowance.
U.S. Appl. No. 11/327,677, Apr. 16, 2010 Amendment after Notice of Allowance.
U.S. Appl. No. 11/327,677, May 10, 2010 Notice of Allowance.
U.S. Appl. No. 11/327,677, May 13, 2010 Response to Amendment under Rule 312.
U.S. Appl. No. 11/446,347, Feb. 26, 2010 Response to Non-Final Office Action.
U.S. Appl. No. 11/446,347, Mar. 15, 2010 Notice of Allowance.
U.S. Appl. No. 11/466,347, May 18, 2010 Amendment after Notice of Allowance.
U.S. Appl. No. 11/446,347, Jun. 2, 2010 Response to Amendment after Notice of Allowance.
U.S. Appl. No. 10/891,624, Mar. 5, 2010 Non-Final Office Action.
U.S. Appl. No. 10/891,624, Jun. 4, 2010 Response to Non-Final Office Action.
U.S. Appl. No. 10/892,034, Aug. 17, 2010 Response to Non-Final Office Action.
U.S. Appl. No. 10/891,624, Jul. 22, 2010 Supplemental Response to Non-Final Office Action.
U.S. Appl. No. 10/891,624, Aug. 30, 2010 Notice of Allowance.
U.S. Appl. No. 10/785,207, Aug. 6, 2010 Response to Final Office Action.
Ebner et al., 2002, Am. J. Clin. Dermatol., vol. 3, No. 6, pp. 427-433.

* cited by examiner

ZINC SALT COMPOSITIONS FOR THE PREVENTION OF DERMAL AND MUCOSAL IRRITATION

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

The present application is a continuation-in-part of pending International Patent Application PCT/US03/03896 filed Feb. 7, 2003, which claimed priority to provisional U.S. Patent Application Ser. No. 60/355,549 filed Feb. 7, 2002, the contents of which are incorporated herein by reference in their entireties.

1. INTRODUCTION

The present invention relates to methods and compositions which employ low concentrations of combinations of zinc salts to prevent the irritation of skin or mucous membranes that may be caused by therapeutic agents, by personal hygiene products, or by various physical, chemical, mechanical, or biological irritants, including infectious agents.

2. BACKGROUND OF THE INVENTION

The Center for Disease Control (CDC) estimates that hospital-acquired infections cost the U.S. healthcare system $4.5 billion a year, and that 80% of these infections are transmitted by direct touch. Although the simple use of soap before and after direct contact with a patient can reduce the transmission of these infections, health care workers often fail to employ this simple measure for several reasons. First, washing with soap and water takes time. Second, such washing necessitates the use of running water, sinks, paper towels and other infrastructural needs that are expensive to provide and maintain and therefore not always immediately accessible by health-care personnel. Thus, most health care workers follow the existing washing guidelines only about 50% of the time.

In response to this problem, the CDC recently issued new hand hygiene guidelines for health care workers. One recommendation is for doctors, nurses and other health care workers to use alcohol-based hand antiseptics rather than traditional water-based soaps to decontaminate their hands between contact with each patient to prevent the spread of infections. This new CDC guideline is expected to reduce the time spent to decontaminate hands and hence increase compliance among health-care workers. Moreover, the recommended alcohol-based products can be carried with the health care worker or installed in several convenient places near patient rooms. The alcohol in the lotion will kill the bacteria, and added emollients should keep the hands soft. Furthermore, the product dries on the hands, so running water, sinks, paper towels, etc. are largely unnecessary.

A product called Avagard™, made by 3M, is commercially available having a combination of emulsifiers, namely Beheneth-10, behenyl alcohol, cetylpalmitate, and diisopropyl dimer dilinoleate with 1% chlorhexidine gluconate solution and 61% ethyl alcohol (w/w).

A product called Prevacare™, made by Johnson & Johnson, is commercially available having 60% ethanol as its active ingredient, water as a vehicle, liposome-building blocks including glycerol distearate, stearate-10, cholesterol, and polysorbate 80, sodium laureth sulfate as a surfactant, propylene glycol as a moisturizer, and preservatives including diazolidinyl urea, methylparaben, and propylparaben. Prevacare-D™ is a commercially available product having 60% ethanol as its active ingredient, and also includes cyclomethicone as an emollient, polyethylene and silica as viscosity builders, mineral oil as a moisturizer/emollient, propylparaben as a preservative and fragrance.

A principal drawback with the increased use of alcohol-based products such as Avagard™, Prevacare™, or others presently available or embodied in various issued U.S. or European patents (see e.g. U.S. Pat. No. 3,485,915, U.S. Pat. No. 4,478,853, U.S. Pat. No. 4,956,170, U.S. Pat. No. 5,403,864, U.S. Pat. No. 5,516,510, U.S. Pat. No. 5,776,430, U.S. Pat. No. 5,885,562, U.S. Pat. No. 5,951,993, U.S. Pat. No. 6,022,551, U.S. Pat. No. 6,107,261, U.S. Pat. No. 6,136,771, U.S. Pat. No. 6,204,230, U.S. Pat. No. 6,352,701, and European Patent Application 0604 848) is that certain ingredients in the formulations, including the alcohol itself, may cause irritation and allergic reactions on the skin. This drawback was readily apparent in a recent study of alcohol-based disinfectants among nurses, which showed that adverse reactions occurred in approximately 12% of all individuals following exposure to these products (Cimiotti et al., 2003, Am. J. Infect. Control 31:43-48.). The instant invention provides one means of overcoming this problem. Certain zinc salts may be added to alcohol-based gels, hand scrubs or other products to prevent the irritation that may otherwise be caused by the alcohol or other active or inactive ingredients that they may contain (see e.g. U.S. Pat. No. 5,965,610 and U.S. Pat. No. 5,985,918, the contents of which are incorporated by reference herein).

Transmission of infectious diseases is also a serious public health concern outside of the health care setting. For example, a growing number of infectious agents may be transmitted by sexual contact, and public health experts increasingly advocate the use of various devices or substances to reduce or prevent the transmission of infectious agents during sexual contact. Unfortunately, such devices or substances often contain irritating components or ingredients that may cause irritation or the dermis or mucous membranes, thereby actually increasing the risk of infection. For example, male or female condoms are often made from latex or other potentially irritating substances. Genital creams, lotions or ointments often contain potentially irritating microbicides, fungicides or spermicides.

In the present invention, specific combinations of two or more water-soluble organic salts of zinc have been identified that are effective in preventing irritation caused by spermicides, microbicides, and alcohol-based gels at concentrations that are low enough so that the risk of zinc toxicity, inactivation of therapeutic compounds, and dermal and/or mucosal irritation are minimized.

It is well known that zinc salts exert numerous biological effects. For example, zinc is essential for normal growth and cognitive development in mammals, and zinc deficiency has been implicated in a host of pathophysiological states in humans, including cognitive impairment, ocular dysfunction, eating, disorders and immune dysfunction among many others.

Considering the myriad effects of zinc in humans, it is unlikely that a single mechanism could account for them all. However, one of the most important functions of zinc in vivo may be as a part of metalloproteins known as "zinc finger" proteins. Zinc finger proteins contain cysteine- and/or histidine-rich domains comprised of an α helix and two B strands in an antiparallel orientation that are held together electrostatically by a divalent zinc cation ($Zn^{2+}$). Zinc finger domains are commonly found on proteins that bind to and interact with RNA or DNA. Because zinc finger proteins are essential regulators of cell proliferation, it is easy to understand, at least superficially, how zinc could be crucial for normal growth and cognitive development, which requires large amounts of cell growth. This same mechanism may also explain why zinc is required for normal immune function, since rapid proliferation of various cellular elements of the immune system, such as T-cells and/or B-cells, occurs in response to the presentation of foreign antigens.

Zinc may also play a less direct and less specific role in immune function and other biological processes. Proteins are comprised of linear chains of amino acids, some of which are positively-charged, some of which are negatively-charged, and some of which are neutral. When such a linear chain is allowed to move freely in three-dimensions, constrained only by the peptidic linkages between the individual amino acids, complex three-dimensional structures result. Proteins may assume unique shapes that allow them to interact with other proteins having complementary shapes, the so-called "lock-and-key" theory of protein-protein interactions. However, due to the distribution of charged amino acids, proteins may also have unique electrical configurations that can govern their interactions with other complexly-charged protein molecules. Zinc ions, by binding to negatively-charged regions exposed on the surface of proteins, may alter the charge configuration of the protein and prevent subsequent protein-protein interactions. One practical consequence of this phenomenon, for example within the context of immune function, may be the ability of zinc ions to block the binding of viruses or other pathogens to specific receptors on the cell surface, thus preventing infection.

This latter mechanism may account for the known properties of zinc salts as anti-irritants. Irritation of the skin may ensue following the binding, either specific or non-specific, or proteinaceous or non-proteinaceous compounds to the epithelial cells comprising the surface layer of the skin or mucosa. A large number of people are known to exhibit irritant dermatitis when their skin is exposed to various chemicals, antiseptics (chlorhexidine, quaternary ammonium compound and chlorinated phenols), disinfectants such as alcohol, biological fluids (urine), latex gloves etc. Zinc salts may prevent irritation by altering the charge configuration of the irritant, thereby preventing its subsequent binding to the underlying tissue.

A number of U.S. patents relate to the incorporation of zinc salts in various gel compositions to prevent irritation. For example, U.S. Pat. No. 5,708,023 discloses the use of a gel wherein zinc gluconate comprises the sole gelling agent as a method of preventing skin irritation. Antimicrobial agents may also be incorporated into these gels. However, the relatively high concentrations of zinc (10% to 50% by weight) found in these gels makes them less desirable for internal use, where the diffusion of the water-soluble zinc salt creates the potential for systemic zinc toxicity, which can be manifested as emesis, irritation and corrosion of the gastrointestinal tract, acute renal tubular necrosis and interstitial nephritis.

U.S. Pat. Nos. 5,965,610 and 6,037,386, both entitled "Composition for inactivating irritants in fluids," also disclose compositions containing water-soluble zinc salts such as zinc gluconate, zinc acetate, zinc sulfate, zinc undecylinate and zinc salicylate for use as anti-irritants. When used at high concentrations, these zinc salts can largely prevent irritant dermatitis. Again, these compositions are less suited to internal use due to their relatively high concentrations of zinc (2% or more of zinc oxide or other zinc salts).

U.S. Pat. No. 5,985,918, entitled "Zinc-based anti-irritant creams," relates the use of organic salts of zinc in anti-irritant creams. In the compositions disclosed in this patent, at least 1% and more preferably 5% or more of zinc salts were needed for the products to be completely effective as anti-irritants.

Apart from the potential for systemic zinc toxicity following the absorption of high concentration water-soluble zinc salts through the skin or mucosa following their use in topical creams or gels, zinc itself may be an irritant at high concentrations. Thus, there is a practical upper limit to the amount of zinc that may be contained within anti-irritant creams and lubricants, especially those designed for internal use. The existence of a practical upper limit on the amount of zinc that is desirable for incorporation into contraceptive or antiseptic creams is further evident from the fact that, through its ability to bind to and subsequently inactivate potential irritants such as the contraceptive or antiseptic agent, the inclusion of high concentrations of zinc salts in these products may render them ineffective for their intended functions.

U.S. Pat. No. 5,980,477 of Kelly, entitled "Genital lubricants with zinc salts as anti-viral additives," relates to the incorporation of water-soluble, organic salts of zinc, at concentrations ranging from 0.5%-30%, into genital lubricants or other similar products to effectuate the inactivation of HIV-1 or other viruses implicated in the spread of sexually-transmitted diseases. At the upper limit of the zinc concentration range, there may be an increased risk of zinc toxicity, as well as the potential for vaginal irritation caused by the direct irritant effects of zinc. The effectiveness of the contraceptive agents also may be compromised (see below). Furthermore, Kelly does not appreciate or describe the beneficial anti-irritant effects of low concentrations of combinations of water-soluble, organic salts of zinc.

In the present invention, specific combinations of two or more water-soluble organic salts of zinc have been identified that are effective in preventing irritation caused by spermicides, microbicides, and alcohol-based gels at concentrations that are low enough so that the risk of zinc toxicity, inactivation of therapeutic compounds, and mucosal irritation are minimized. The incorporation of zinc salt combinations into contraceptive or antiseptic lubricants or creams will thus render these products less irritating to the underlying mucosa, and therefore better able to protect against the contraction of infectious diseases, while maintaining the effectiveness of these products for their intended use.

3. SUMMARY OF THE INVENTION

The present invention relates to combinations of water-soluble zinc salts which, when intermixed with gels, creams, lotions or ointments that are then applied to the skin or other surface, can minimize or prevent irritation to the skin. When added to water- or alcohol-based topical disinfectants, the anti-irritant properties of the zinc salts described herein may increase the use of topical disinfectants containing zinc salts among health care workers, thereby reducing the transmission of infectious diseases in hospital settings. These same zinc salt combinations may be added to gels, creams or lubricants containing spermicides, microbicides, fungicides or other potentially-irritating therapeutic agents, to reduce or prevent the irritation of skin or mucosal membranes caused by these therapeutic agents. When employed in genital lubricants, the reduction in irritation of the vaginal mucosa may assist in minimizing the spread of sexually-transmitted diseases.

The invention is based, at least in part, on the following two discoveries. First, the addition of combinations of low concentrations of water-soluble organic salts of zinc to gels, creams, lotions or ointments applied topically were found to increase the ability of these products to prevent irritants from achieving contact with the underlying skin, thus reducing irritation. Second, the addition of combinations of low concentrations of water-soluble organic zinc salts to genital lubricants were observed to reduce the irritation of mucous membranes caused by the presence of potentially-irritating substances such as spermicides, microbicides, fungicides or other therapeutic agents within the lubricant.

4. DETAILED DESCRIPTION OF THE INVENTION

The present invention relates to methods and compositions for the prevention of the irritation of skin or mucosal surfaces that may occur following exposure to irritant substances. It is based, at least in part, on the discovery that the addition of combinations of water-soluble, organic salts of zinc to gels, creams, lotions, or ointments can increase the ability of these gels, creams, lotions or ointments to prevent irritants from causing irritation of the underlying substrate. While it had been found previously that high concentrations of zinc salts added to gels, creams, lotions or ointments may enhance the protective effects of these products, zinc itself at high concentrations has been shown to produce irritation. Furthermore, high concentrations of zinc ions in these products also raise the potential for local or systemic zinc toxicity in subjects who use these products. One surprising aspect of the instant invention, therefore, is the finding that low concentrations of zinc salts, especially when two or more such salts are used in combination, can achieve a satisfactory degree of anti-irritant effect while minimizing the potential for both zinc-induced irritation and toxicity. A further advantage of the present approach is that the concentrations of the combination of zinc salts advocated in the present invention are sufficiently low so that their addition to gels, creams, lotions or ointments containing biologically-active agents such as spermicides, microbicides, fungicides or other potentially-irritating therapeutic compounds may not be expected to result in the inactivation of these compounds, thereby permitting their use as anti-irritant agents in gels, creams, lotions or ointments containing these compounds.

Accordingly, in various embodiments, the present invention provides for anti-irritant gels, creams, lotions or ointments comprising low concentrations of two or more water-soluble, organic salts of zinc that are effective in preventing or reducing irritation.

The term "low concentration" means percentages of free zinc ions ($Zn^{2+}$) in the gel, cream, lotion or ointment at less than 0.5% on a weight to weight (w/w) basis.

Suitable zinc salts for use in these compositions include zinc acetate (molar solubility in water of 1.64 moles/l), zinc butyrate (molar solubility in water of 0.4 moles/l), zinc citrate (molar solubility in water of <0.1 moles/l), zinc gluconate (molar solubility in water of 0.28 moles/l), zinc glycerate (moderately water soluble), zinc glycolate (moderately water soluble), zinc formate (molar solubility in water of 0.33 moles/l), zinc lactate (molar solubility in water of 0.17 moles/l), zinc picolinate (moderately water soluble), zinc proprionate (molar solubility in water of 1.51 moles/l), zinc salicylate (low water solubility), zinc tartrate (moderately water soluble) and zinc undecylenate (moderately water soluble).

The terms "prevention" or "reduction" of irritation means a decrease in objective or subjective signs of irritation in tissues treated with the gels, creams, lotions or ointments comprising low concentrations of two or more water-soluble, organic salts of zinc of at least 50%, and more preferably by greater than 90% relative to control tissues exposed to the irritant agent and the same gels, creams, lotions or ointments lacking zinc salts. Irritation in this context may be evidenced by redness or other changes in coloration, inflammation or swelling, hypersensitivity, the occurrence of burning, itching or other painful stimuli, or other macroscopic or microscopic changes known to those of ordinary skill in the art to be associated with irritation.

The gels, creams, lotions or ointments of the invention may be applied topically to the skin or to the various mucous membranes of the body, including but not limited to those or the oral, nasal, vaginal or rectal cavities, to prevent the effects of exogenous irritants upon these surfaces.

In preferred embodiments, the gel or cream comprises a mixture of water, a gelling agent, a thickening agent, a hydrophilic or hydrophobic polymer, an emulsifying agent, and an emollient. The zinc salts comprise a combination of effective amounts of two or more of the following: zinc acetate (0.1-2.0%), zinc citrate (0.1-2.0%), zinc gluconate (0.1-2.0%) and zinc lactate (0.1-2.0%). In preferred embodiments, the zinc salts are 1% zinc gluconate, 0.2% or 0.4% zinc acetate and 0.2% of either zinc lactate or zinc citrate.

In alternative embodiments, the gel comprises a mixture of water (10-50%), alcohol (30-90%), a zinc gel (a combination of quaternary cationic hydroxy ethyl cellulose (0.1-0.3%) and triple zinc salt mixture containing zinc gluconate (0.1-2.0%), zinc acetate (0.1-2.0%) and zinc lactate (0.05-2.0%)) and emollients (0.3-1%).

In further embodiments, the cream comprises a mixture of water (10-50%), petroleum jelly (10-40%), crothix (0.5-3%), allantoin (0.3-1.0%), salicylic acid (1.0-4.0%), dimethicone (0.5-5.0%), zinc stearate (1.0-5.0%), zinc oxide (0.5-5.0%), a triple zinc salt mixture containing zinc gluconate (0.1-2.0%), zinc acetate (0.1-2.0%) and zinc lactate (0.05-2.0%), and other emollients (10-30%).

In further embodiments, the lotion comprises a mixture of water (60-80%), petroleum jelly (2-10.0%), crothix (0.5-2.0%), crodomol MM (0.5-2.01%), cremerol (0.5-2.0%), zinc stearate (1.0-5.0%), zinc oxide (0.1-3.0%), a triple zinc salt mixture containing zinc gluconate (0.05-2.0%), zinc acetate (0.05-2.0%) and zinc lactate (0.05-2.0%), and emollients (10-30%). In preferred embodiments, the zinc salts are 0.3% zinc gluconate, 0.1% zinc acetate and 0.1% of zinc lactate.

The present invention further relates to hydroalcoholic gel compositions comprising combinations of 1% or less of hydrogel dissolved in water at ambient temperature and 3% or less of emollient dissolved in alcohol or 3% or less of emulsifier wherein said compositions have viscosities below 4000 centipoise (cps) at between 20-40° C. These percentages and further percentages discussing these hydroalcoholic gel compositions should be considered weight/weight percentages, unless otherwise specified. In preferred embodiments of the invention such compositions comprise 30-80% alcohol, 15-70% water, 0.05-0.5% hydrogel, and 0.2-3.0% emollient and/or 0.05-0.5% emulsifier with viscosities of less than 2000 cps, most preferably between 50-500 cps. Additional embodiments of this invention further include silicone polymer, emollient solvent, antimicrobial agent, and thickening agent, while maintaining the low viscosities as preferred.

In any of the embodiments described above, the emollients may include PEG 20 almond glycerides, Probutyl DB-10, Glucam P-20, Glucam E-10, Glucam P-10, Glucam E-20, Glucam P-20 distearate, glycerin, propylene glycol, cetyl acetate, and acetylated lanolin alcohol, cetyl ether, myristyril ether, hydroxylated milk glycerides, polyquatemium compounds, copolymers of dimethyl dialyl ammonium chloride and acrylic acid, dipropylene glycol methyl ethers, polypropylene glycol ethers and silicon polymers. Other suitable emollients may include hydrocarbon-based emollients such as petrolatum or mineral oil, fatty ester-based emollients, such as methyl, isopropyl and butyl esters of fatty acids such as isopropyl palmitate, isopropyl myristate, isopropyl isostearate, isostearyl isostearate, diisopropyl sebacate, and propylene dipelargonate, 2-ethylhexyl isononoate, 2-ethylhexyl stearate, $C_{12}$-$C_{16}$ fatty alcohol lactates such as cetyl lactate and lauryl lactate, isopropyl lanolate, 2-ethylhexyl salicylate, cetyl myristate, oleyl myristate, oleyl stearate, oleyl oleate, hexyl laurate, and isohexyl laurate. Additional useful emollients include lanolin, olive oil, cocoa butter, and shea butter.

In any of the embodiments described above, the gel, cream, lotion or ointment may also contain stabilizing agents consisting of antioxidants (0.2-1%), including but not limited to vitamin C (ascorbic acid) and vitamin E (tocopherol), and surfactants (0.2-1.0%), including but not limited to incromide or silicone-based surfactants (Masil SF-19, BASE). The stabilizing agents surprisingly remove the turbidity of the gel, cream, lotion or ointment, resulting in a clear product that imparts a light feel to the surface to which it is applied.

In any of the embodiments described above, the gel, cream, lotion or ointment may also contain thickening agents (0.6-2%) such as stearyl alcohol, cationic hydroxy ethyl cellulose (Ucare; JR30), hydroxy propyl methyl cellulose, hydroxy propyl cellulose (Klucel), chitosan pyrrolidone carboxylate (Kytamer), behenyl alcohol, zinc stearate, and emulsifying waxes, including but not limited to Incroquat and Polawax. Other thickening and/or gelling agents suitable for incorporation into the anti-irritant gels, creams, lotions or ointments described herein include, for example, an addition polymer of acrylic acid, a resin such as Carbopol® ETD™ 2020, guar gum, acacia, acrylates/steareth-20 methacrylate copolymer, agar, algin, alginic acid, ammonium acrylate co-polymers, ammonium alginate, ammonium chloride, ammonium sulfate, amylopectin, attapulgite, bentonite, C9-15 alcohols, calcium acetate, calcium alginate, calcium carrageenan, calcium chloride, caprylic alcohol, carbomer 910, carbomer 934, carbomer 934P, carbomer 940, carbomer 941, carboxymethyl hydroxyethyl cellulose, carboxymethyl hydroxypropyl guar, carrageenan, cellulose, cellulose gum, cetearyl alcohol, cetyl alcohol, corn starch, damar, dextrin, dibenzlidine sorbitol, ethylene dihydrogenated tallowamide, ethylene diolamide, ethylene distearamide, gelatin, guar gum, guar hydroxypropyltrimonium chloride, hectorite, hyaluronic acid, hydrated silica, hydroxybutyl methylcellulose, hydroxyethylcellulose, hydroxyethyl ethylcellulose, hydroxyethyl stearamide-MIPA, isocetyl alcohol, isostearyl alcohol, karaya gum, kelp, lauryl alcohol, locust bean gum, magnesium aluminium silicate, magnesium silicate, magnesium trisilicate, methoxy PEG-22/dodecyl glycol copolymer, methylcellulose, microcrystalline cellulose, montmorillonite, myristyl alcohol, oat flour, oleyl alcohol, palm kernel alcohol, pectin, PEG-2M, PEG-5M, polyacrylic acid, polyvinyl alcohol, potassium alginate, potassium aluminium polyacrylate, potassium carrageenan, potassium chloride, potassium sulfate, potato starch, propylene glycol alginate, sodium acrylate/vinyl alcohol copolymer, sodium carboxymethyl dextran, sodium carrageenan, sodium cellulose sulfate, sodium chloride, sodium polymethacylate, sodium silicoaluminate, sodium sulfate, stearalkonium bentotnite, stearalkonium hectorite, stearyl alcohol, tallow alcohol, TEA-hydrochloride, tragacanth gum, tridecyl alcohol, tromethamine magnesium aluminium silicate, wheat flour, wheat starch, xanthan gum, abietyl alcohol, acrylinoleic acid, aluminum behenate, aluminum caprylate, aluminum dilinoleate, aluminum salts, such as distearate, and aluminum isostearates, beeswax, behenamide, butadiene/acrylonitrile copolymer, C29-70 acid, calcium behenate, calcium stearate, candelilla wax, carnauba, ceresin, cholesterol, cholesterol hydroxystearate, coconut alcohol, copal, diglyceryl stearate malate, dihydroabietyl alcohol, dimethyl lauramine oleate, dodecanoic acid/cetearyl alcohol/glycol copolymer, erucamide, ethylcellulose, glyceryl triacetyl hydroxystearate, glyceryl tri-acetyl ricinolate, glycol dibehenate, glycol di-octanoate, glycol distearate, hexanediol distearate, hydrogenated C6-14 olefin polymers, hydrogenated castor oil, hydrogenated cottonseed oil, hydrogenated lard, hydrogenated menhaden oil, hydrogenated palm kernel glycerides, hydrogenated palm kernel oil, hydrogenated palm oil, hydrogenated polyisobutene, hydrogenated soybean oil, hydrogenated tallow amide, hydrogenated tallow glyceride, hydrogenated vegetable glyceride, hydrogenated vegetable oil, Japan wax, jojoba wax, lanolin alcohol, shea butter, lauramide, methyl dehydroabietate, methyl hydrogenated rosinate, methyl rosinate, methylstyrene/vinyltoluene copolymer, microcrystalline wax, montan acid wax, montan wax, myristyleicosanol, myristyloctadecanol, octadecene/maleic anhyrdine copolymer, octyldodecyl stearoyl stearate, oleamide, oleostearine, ouricury wax, oxidized polyethylene, ozokerite, paraffin, pentaerythrityl hydrogenated rosinate, pentaerythrityl tetraoctanoate, pentaerythrityl rosinate, pentaerythrityl tetraabietate, pentaerythrityl tetrabehenate, pentaerythrityl tetraoleate, pentaerythrityl tetrastearate, ophthalmic anhydride/glycerin/glycidyl decanoate copolymer, ophthalmic/trimellitic/glycols copolymer, polybutene, polybutylene terephthalate, polydipentene, polyethylene, polyisobutene, polyisoprene, polyvinyl butyral, polyvinyl laurate, propylene glycol dicaprylate, propylene glycol dicocoate, propylene glycol diisononanoate, propylene glycol dilaurate, propylene glycol dipelargonate, propylene glycol distearate, propylene glycol diundecanoate, PVP/eiconsene copolymer, PVP/hexadecene copolymer, rice bran wax, stearlkonium bentonite, stearalkonium hectorite, stearamide, stearamide DEA-distearate, stearamide DIBA-stearate, stearamide MEA-stearate, stearone, stearyl erucamide, stearyl stearate, stearyl stearoyl stearate, synthetic beeswax, synthetic wax, trihydroxystearin, triisononanoin, triisostearin, tri-isostearyl trilinoleate, trilaurin, trilinoleic acid, trilinolein, trimyristin, triolein, tripalmitin, tristearin, zinc laurate, zinc myristate, zinc neodecanoate, zinc rosinate, and mixtures thereof.

In any of the embodiments described above, the gel, cream, lotion or ointment may also contain phenoxyethanol (0.3-1.0%) as a solubilizing agent.

In any of the embodiments described above, the gel, cream, lotion or ointment may also contain a humectant, such as, for example, glycerin, 1-2-propylene glycol, dipropylene glycol, polyethylene glycol, 1,3-butylene glycol, or 1,2,6-hexanetriol.

In any of the embodiments described above, the gel, cream, lotion or ointment may also contain antimicrobials (0.05-2%) consisting of biguanides, quaternary ammonium chlorides, or chlorinated phenols. Examples of suitable anti-microbial agents include, but are not limited to, chlorhexidine gluconate (CHG), benzalkonium chloride (BZK), or iodopropynylbutyl carbamate (IPBC; Germall plus).

In any of the embodiments described above, the gel, cream, lotion or ointment may also contain neutralizing agent to neutralize carboxyl groups present in one or more other component, such as carboxyl groups in a thickening agent. Suitable neutralizing agents include diisopropylamine and triethanolamine.

In any of the embodiments described above, the gel, cream, lotion or ointment may also contain a surfactant. The surfactant may be an anionic surfactant, a cationic surfactant, an ampholytic surfactant, or a nonionic surfactant. Examples of nonionic surfactants include polyethoxylates, fatty alcohols (e.g., ceteth-20 (a cetyl ether of polyethylene oxide having an average of about 20 ethylene oxide units) and other "BRIJ"® nonionic surfactants available from ICI Americas, Inc. (Wilmington, Del.)), cocamidopropyl betaine, alkyl phenols, fatty acid esters of sorbitol, sorbitan, or polyoxyethylene sorbitan. Suitable anionic surfactants include ammonium lauryl sulfate and lauryl ether sulfosuccinate. A preferred surfactant is lauroyl ethylenediamine triacetic acid sodium salt at a concentration between about 0.5-2.0%. Suitable concentrations of surfactant are between about 0.05% and 2%.

Water used in the formulations described herein is preferably deionized water having a neutral pH. When used in hydroalcoholic gel compositions, the concentration of water should be suitable to dissolve the hydrogels according to the invention.

In any of the embodiments described above, the gel, cream, lotion or ointment may also contain additional additives, including but not limited to a silicone fluid (such as dimethicone or cyclomethicone), dyes, fragrances, etc. Examples of additional additives include but are not limited to: pH adjusters, including basic pH adjusters such as ammonia, mono-, di- and tri-alkyl amines, mono-, di- and tri-alkanolamines, alkali metal and alkaline earth metal hydroxides (e.g., ammonia, sodium hydroxide, potassium hydroxide, lithium hydroxide, monoethanolamine, triethylamine, isopropylamine, diethanolamine and triethanolamine); acid pH adjusters such as mineral acids and polycarboxylic acids (e.g., hydrochloric acid, nitric acid, phosphoric acid, sulfuric acid, citric acid, glycolic acid, and lactic acid); vitamins such as vitamin A, vitamin E and vitamin C; polyamino acids and salts, such as ethylenediamine tetraacidic acid (EDTA), preservatives such as Germall plus and DMDM hydantoin, and sunscreens such as aminobenzoic acid, arobenzone, cinoxate, diioxybenzone, homosalate, menthyl anthranilate, octocrylene, octyl methoxycinnamate, octyl salicylate, oxybenzoate, padimate O, phenylbenzimidazole, sulfonic acid, sulisobenzone, titanium dioxide, trolamine salicylate and zinc oxide.

In any of the embodiments described above, the gel, cream, lotion or ointment may also contain essential oils (EO), which are volatile oils obtained from plant or animal sources and are composed of complex mixtures of several constituents as monoterpenes and sesquiterpene hydrocarbons, monoterpene and sesquiterpene alcohols, esters, ethers, aldehydes, ketones, oxides and the like, or fragrance and flavor (FF) chemicals. Examples of these EO and FF include, but are not limited to, almond oil, ylang-ylang oil, neroli oil, sandalwood oil, frankincense oil, peppermint oil, lavender oil, jasmine absolute, geranium oil bourbon, spearmint oil, clove oil, lemongrass oil, cedarwood oil, balsam oils, tangerine oil, 1-citronellol, α-amylcinnamaldehyde, lyral, geraniol, farnesol, hydroxycitronellal, isoeugenol, eugenol, eucalyptus oil and eucalyptol, lemon oil, linalool, and citral. Apart from their effects as fragrances or flavorants, such compounds also may be useful in the instant invention as anti-microbial agents.

A hydrogel, as used herein, includes hydroxypropylmethyl cellulose, cationic hydroxyethyl cellulose (U-care polymers), ethyl cellulose, hydroxypropyl cellulose, hydroxymethyl cellulose, carboxy methyl cellulose, polyethylene oxide (polyox resins), and chitosan pyrrolidone carboxylate (Kytomer PC). These hydrogels preferably do not bind to any added antimicrobial agent, therefore leaving the optionally added antimicrobial agent free for rapid and long-term activity. In addition, it has been discovered that alcohol used to form the hydroalcoholic gel is not trapped in the hydroalcoholic gel composition and is therefore available for rapid and long-term action. The hydrogel is present in a concentration between 0.1-1.0%, and preferably is a cationic hydroxyethyl cellulose (U-care polymers) in a concentration between 0.05-0.5%, most preferably 0.2%.

Alcohols that may be used according to this invention relating to hydroalcoholic gel compositions include preferably aliphatic alcohols, including, but not limited to, ethanol, isopropyl alcohol, n-propyl alcohol, and mixtures thereof; fatty alcohols, including, but not limited to, cetyl alcohol, myristol alcohol, stearyl alcohol, octyl alcohol, decyl alcohol and lauryl alcohol, and mixtures thereof; and hexanol. The concentration of alcohol may be between 30% and 95%, preferably between 40% and 70%; preferably the aliphitic alcohols is ethanol or isopropyl alcohol at a concentration between and 60% and 95%; when present, the concentration of fatty alcohols is preferably between 0.5% and 5.0%; and, when present, the concentration of hexanol is preferably between 3% and 10%, more preferably 5%.

An emollient and/or humectant (collectively referred to hereinafter as emollients), as used according to this invention relating to hydroalcoholic gel compositions, include the emollients and humectants discussed above, and preferably include one or more than one PPG 20 Almond Glycerides, Probutyl DE-10, Glucam P20, Glucam E-10, Glucam P-10, Glucam E-20, Glucam P-20 distearate, glycerin, propylene glycol, octoxyglycerin (Sensiva), cetyl acetate and acetylated lanolin alcohol (Acetulan), cetyl ether (PPG-10), myristyl ether (PPG-3), hydroxylated milk glycerides (Cremerol HMG), polyquaternium compounds (U-care compounds), chitosan (Kytamer), copolymer of dimethyl dialyl ammonium chloride and acrylic acid (Merquat), dipropylene glycol methyl ethers (Dowanol DPM Dow Corning), and polypropylene glycol ethers (Ucon 50-HB-660, Union Carbide). Preferably the emollient is present at a concentration of 3% or less, such that the viscosity of the composition is preferably less than 2000 centipoise at 20-40° C., more preferably between 0.2 and 3%.

Surfactants and/or emulsifiers (collectively referred to hereinafter as emulsifiers), as used according to this invention relating to hydroalcoholic gel compositions, include the emulsifiers and surfactants discussed above, and preferably include non-ionic or cationic self-emulsifying waxes that are preferably soluble in alcohol at ambient temperature including Incroquat Behenyl TMS, Incroquat Behenyl TMS-50, Polawax, stearyl alcohol and cetearyl alcohol. These emulsifiers are present at a concentration between 0.05-3.0%. Emulsifiers to this invention preferably include Incroquat Behenyl TMS, which is a mild cationic emulsifier as well as an excellent conditioner, and Polawax, which is a non-ionic self emulsifying wax, individually at a concentration of between 0.05-0.5%, and in combination at a concentration of between 0.05-0.5%, more preferably in combination at a concentration ratio of approximately 1:1. If more than one emulsifier is used, it is preferred that the total concentration of all of the emulsifier is between 0.05-0.5% of the total concentration.

Silicone polymer, as used according to this invention relating to hydroalcoholic gel compositions, preferably includes one or more than one polydimethylsiloxane polymer (Dow Corning 225 Silicone Fluid), dimethiconol fluid in dimethicone (Dow Corning 1403 Silicone Fluid), cyclomethicone and dimethicone copolyl (Dow Corning 3225C Silicone Fluid), and silicone glycol (BASF 1066 DCG polyol). Suitable concentrations of silicone polymer are between about 0.1-1.0%.

Emollient solvents include, but are not limited to, one or more than one glycidyl ethers having alkyl chains up to and including 18 carbon molecules and ethoxylates and propoxylates thereof, glyceryl ethers having alkyl chains up to and including 18 carbon molecules and ethoxylates and propoxylates thereof, mono- and diglyceryl ethers having alkyl chains up to and including 18 carbon molecules and ethoxylates and propoxylates thereof, ethoxylate and propoxylate ethers, ethoxy diglycol esters, ethyl hexyl alcohol propoxylate, and propylene glycol esther ethoxylates and propoxylates, and preferably Arlamol (Atlas). Suitable concentrations of emollient solvent are between 0.5-5%.

Thickening agents that may be used according to this invention relating to hydroalcoholic gel compositions include the thickening agents and gelling agents discussed above, preferably behenyl alcohol, crodomol, and crothix. Suitable concentration of thickening agent are between 0.05-10%. Gelling agents such as Caropol are not preferred due to their high viscosity and their requiring neutralizing agents to neutralize the gelling agent with alkaline materials.

Antimicrobial agents that may be used in addition to the hydroalcoholic gel composition according to the invention include, but not limited to, one or more than one biguanide, phenol, quaternary ammonium compound and anti-fungal agent. Preferably, the concentration of the one or more than one antimicrobial agent is less than 3%. More than one antimicrobial agent may be used in combination, such as chlorhexidine gluconate, benzalkonium chloride and phenoxyethanol, preferably at a concentration of between 0.05-0.5%, 0.1-0.25%, and 0.1-1.0%, respectively. Because cationic antimicrobials, such as biguanides and quaternary ammonium compounds, can bind to the surface of the skin, they may not be available to inactivate pathogens that come into contact with the skin. The gel formulation according to the invention forms a film on the surface of the hand when applied, which film acts as a barrier preventing the antimicrobial agents that may be added to the gel from binding to the surface of the skin.

Ambient temperature is defined herein between 20 and 35° C. Room temperature is defined herein between 20 and 25° C.

The present invention further provides for spermicidal gels, creams, lotions or ointments containing low concentrations of two or more water-soluble, organic salts of zinc that are effective in reducing or preventing the irritation caused by the spermicidal agent. Such gels, creams, lotions or ointments may be applied topically to the skin of the penis, the vaginal mucosa, or to the surface of latex articles such as male or female condoms, to prevent the irritating effects of spermicides that are incorporated into the gel. These products have the additional advantage of minimizing or preventing irritation caused by allergic reaction to latex. Spermicidal agents are well known to those of ordinary skill in the art, and include, but are not limited to, detergent-based spermicides. In a preferred embodiment, the spermicide is nonoxynol-9 and the zinc salts comprise a combination of two or more of the following: zinc acetate (0.1-0.3%), zinc citrate (0.1-0.3%), zinc gluconate (0.1-2.0%) and zinc lactate (0.1-0.3%). In a preferred embodiment, the zinc salts are 0.3% zinc gluconate, 0.1% zinc acetate and 0.1% zinc lactate.

In related and overlapping embodiments, the invention provides for anti-microbial gels, creams, lotions or ointments containing low concentrations of two or more water-soluble, organic salts of zinc that are effective in reducing or preventing the irritation caused by the anti-microbial agent. Such gels, creams, lotions or ointments may be applied topically to the skin or to various mucosal surfaces of the body to prevent or minimize infection. These products have the additional advantage of reducing or preventing irritation that may be caused by the anti-microbial agent that is present in the gel, cream, lotion or ointment. Such anti-microbial agents include, but are not limited to, anti-viral, anti-bacterial, or anti-fungal substances.

Anti-microbial agents also include substances possessing any combination of viricidal or viristatic, bacteriocidal or bacteriostatic, or fungicidal or fungistatic properties. Anti-microbial agents are well known to those of ordinary skill in the art. Examples of anti-microbial agents include, but are not limited to, iodophors, iodine, benzoic acid, dihydroacetic acid, propionic acid, sorbic acid, methyl paraben, ethyl paraben, propyl paraben, butyl paraben, cetrimide, benzalkonium chloride, dequalinium chloride, chlorhexidine, chloroeresol, chlorxylenol, benzyl alcohol, bronopol, chlorbutanol, ethanol, phenoxyethanol, phenylethyl alcohol, 2,4-dichlorobenzyl alcohol, thiomersal, clindamycin, erythromycin, benzoyl peroxide, mupirocin, bacitracin, polymyxin B, neomycin, triclosan, parachlorometaxylene, foscamet, miconazole, fluconazole, itriconazole, ketoconazole, and pharmaceutically acceptable salts thereof. As indicated above, certain EO and FF chemicals also may possess anti-microbial activities. These and further examples of anti-microbial agents useful in this invention can be found in such references as Goodman and Gilman's The Pharmacological Basis of Therapeutics (Goodman Gilman A, Rail T W, Nies A S, Taylor P, ed. (Pergamon Press; Elmsford, N.Y.: 1990)), the contents of which are hereby incorporated by reference.

Pharmaceutically acceptable chlorhexidine salts are well known to those of ordinary skill in the art and include, but are not limited to, chlorhexidine palmitate, chlorhexidine diphosphanilate, chlorhexidine digluconate, chlorhexidine diacetate, chlorhexidine dihydrochloride, chlorhexidine dichloride, chlorhexidine dihydroiodide, chlorhexidine diperchlorate, chlorhexidine dinitrate, chlorhexidine sulfate, chlorhexidine sulfite, chlorhexidine thiosulfate, chlorhexidine di-acid phosphate, chlorhexidine difluorophosphate, chlorhexidine diformate, chlorhexidine dipropionate, chlorhexidine di-iodobutyrate, chlorhexidine di-n-valerate, chlorhexidine dicaproate, chlorhexidine malonate, chlorhexidine succinate, chlorhexidine malate, chlorhexidine tartrate, chlorhexidine dimonoglycolate, chlorhexidine monodiglycolate, chlorhexidine dilactate, chlorhexidine di-α-hydroxyisobutyrate, chlorhexidine diglucoheptonate, chlorhexidine di-isothionate, chlorhexidine dibenzoate, chlorhexidine dicinnamate, chlorhexidine dimandelate, chlorhexidine di-isophthalate, chlorhexidine di-2-hydroxynapthoate, and chlorhexidine embonate. Chlorhexidine free base is a further example of an anti-microbial agent.

In a preferred embodiment, the anti-microbial agent is 1% chlorhexidine and the zinc salts comprise a combination of at least two or more of the following: zinc acetate (0.1-2.0%), zinc citrate (0.1-2.0%), zinc gluconate (0.1-2.0%) and zinc lactate (0.1-2.0%). In another preferred embodiment, the anti-microbial agent is 2% miconazole and the zinc salts comprise a combination of at least two or more of the following: zinc acetate (0.1-2.0%), zinc citrate (0.1-2.0%), zinc gluconate (0.1-2.0%) and zinc lactate (0.1-2.0%).

In formulating compositions of this invention it is contemplated that the formulations may further comprise ingredients which, while not having the activity of the above-named ingredients, will aid in the formulation and use of the composition as a whole. Examples of such ingredients are well-known to those of ordinary skill in the art of producing formulations for biological purposes. Examples of these ingredients include such substances as binders, emollients, preservatives (such as methyl paraben), lubricants, colorants, perfumes, and the like. Accordingly, when the surface contemplated is skin, the composition of this invention may contain ingredients which are added to known lotions or medicaments, which are physiologically acceptable to skin and which do not contain ingredients which will reverse or retard the action of the irritant-inactivating agent.

Alternatively, the composition may be added to pre-existing formulations provided that the ingredients in those formulations do not prevent or retard the activity of the claimed composition. In a preferred embodiment, the claimed composition can be added to creams and lotions which are commercially available. Examples of commercially available lubricants include, but are not limited to, those lubricants sold under the tradenames "KY JELLY," "ASTROGLIDE," and "PREVACARE." Examples of commercially available lotions include, but are not limited to, those lotions sold under the tradenames "SOFT-SENSE," "LOTION SOFT," "CUREL," and "KERI". SOFT-SENSE (Johnson & Son, Inc., Racine, Wis.) is known to contain purified water, glycerin USP, distearyldimonium chloride, petrolatum USP, isopropyl palmitate, 1-hexadecanol, tocopheryl acetate (vitamin E USP), dimethicone, titanium dioxide USP, methyl paraben, propyl paraben, sodium chloride, and fragrance. LOTION SOFT (Calgon Vestal, St. Louise, Mo.) is a nonionic moisturizing lotion which is known to contain mucopolysaccharide. CUREL (Bausch & Lomb Incorporated, Rochester, N.Y.) is known to contain deionized water, glycerin, quatemium-5, petrolatum, isopropyl palmitate, 1-hexadecanol, dimethicone, sodium chloride, fragrance, methyl paraben, and propyl paraben.

The invention provides for methods of using the foregoing compositions to prevent irritation to an epithelial tissue (e.g. a mucosal tissue or the skin) comprising applying an effective amount of the composition to the surface. Examples of irritants against which protection may be afforded include, but are not limited to, those induced by physcial, chemical, mechanical or biological irritants. Specific examples of the foregoing irritants include, but are not limited to, means for hair removal (e.g. depilatories, waxing and razors), hair relaxants (e.g. sodium hydroxide, calcium hydroxide, thioglycolates), antiperspirants (e.g. aluminum chlorhydrate and other aluminium salts), dermatological treatments (e.g. alpha hydroxy acids (AHAs), especially glycolic and trichloroacetic acids), keratoyltic skin-irritating conditions (e.g. psoriasis, dandruff, etc.), infectious skin irritants (e.g. bacteria and fungi), and agents applied for therapeutic purposes. The epithelial surface to be protected from irritation may be dermal or mucosal, including vaginal, anorectal, oral or nasal.

The invention further provides for methods of protecting against infection comprising applying, to an epithelial tissue such as the skin or a mucous membrane of the body, an effective amount of one of the foregoing compositions which inhibits irritation of the tissue. Examples of infectious agents against which protection may be afforded include, but are not limited to, Human Immunodeficiency Virus (HIV), Human Papilloma Virus (HPV), Herpes Simplex Virus (HSV), Chlamydia trachomatis, Neisseria gonorrhoea, Trichomonas vaginalis, and Candida albicans.

5. WORKING EXAMPLES

5.1. Example 1

Evaluation of the Anti-Irritant Effect of Various Zinc Salts in a Gel Base as a Barrier to Irritants Using Chlorophyllin Dye as the Test Model Chlorophyllin is a dye that stains the skin a deep green color. The stain can only be removed after several washes with soap and water. After application of a gel base (55% Propylene glycol, 44.6% Water, 0.4% Xanthum gum) containing various combinations of zinc salts (Table 1) to the skin of human volunteers, the extent of penetration of externally-applied chlorophyllin dye through the gel formulations was determined.

In these studies, the forearms of the human volunteers were washed with soap and water and then dried. The gel formulation to be tested (0.1 g) was spread over a 4 cm by 4 cm area of the forearm and allowed to dry for 5 minutes. A 3 cm by 3 cm square of paper towel (Marcal™) was dipped in a 1.5% aqueous solution of chlorophyllin and placed centrally on the area of the skin to which the gel had been applied. The site was then covered by plastic wrap which was immobilized via surgical tape placed around its edges.

After 1 hour, the plastic and paper toweling were removed and the forearm was dried with a tissue by rubbing five times. An "anti-irritant" score was assigned based on the degree of coloration of the skin by the dye. The degree of coloration was scored as follows: 0=no color, 1=slight color, 2=moderate color, 3=heavy coloration. The site was then rinsed under lukewarm water while rubbing ten times and a post-wash score was read. After rinsing with soap and water and drying by blotting with dry tissue, the tests areas were scored again. The average of these three scores for each condition is shown in Table 1. From these studies, the combination of 1% zinc gluconate, 0.2% zinc acetate and 0.2% zinc lactate is superior to all single zinc salts and to other zinc salt combinations in preventing the penetration of the dye through the lubricant base and its binding to the surface of the skin.

TABLE 1

Inhibition of Chlorophyllin Penetration by Zinc Salts

| Zinc salts in lubricant base* | Scoring of coloration |
|---|---|
| 2.0% zinc gluconate | 0.5 |
| 1.4% zinc gluconate | 1.0 |
| 0.6% zinc gluconate | 1.0 |
| 1.4% zinc lactate | 1.5 |
| 1.4% zinc acetate | 0.5 |
| 1.4% zinc citrate | 1.0 |
| 1.0% zinc gluconate + 0.4% zinc acetate | 0.5 |
| 1.0% zinc gluconate + 0.2% zinc acetate + 0.2% zinc lactate | 0.1 |
| 1.0% zinc gluconate + 0.2% zinc acetate + 0.2% zinc citrate | 0.2 |
| 0.6% zinc acetate + 0.8% zinc lactate | 1.0 |
| Control (lubricant base only) | 3.5 |

*The necessary amount of lubricant base was added to each sample to achieve 100 g.

5.2. Example 2

Evaluation of the Anti-Irritant Effect of Zinc Salt-Containing Gel-based Lubricant Composition using a Strong Skin Irritant on a Volunteer Methyl salicylate is the active ingredient in Ben-gay™ lotion. This compound is known to be an irritant in certain individuals. A volunteer who exhibits an allergic reaction to methyl salicylate was used as a test subject to evaluate the ability of gel bases containing various zinc salt compositions to prevent methyl salicylate-mediated irritation.

In this study, 10% of Ben-gay™ lotion was mixed with 90% of lubricant (base composition was the same as in Example 1 containing various zinc salt formulations (Table 2) and 0.2 gram per site was applied at three different sites located on the left and right forearms of the volunteer for a total of six sites. After 5 min, the site was wiped with a dry tissue to remove the gel formulation and the degree of irritation was noted. Irritation was defined as the presence of redness, which was scored as follows: 0=no redness, 1=slight redness, 2=moderate redness, 3=heavy redness. The presence of a burning sensation, if any, was also noted. The results of these studies are shown in Table 2.

TABLE 2

Reduction of Skin Irritation by Zinc Salts

| Zinc salt formulation | Scoring of skin reaction (redness) |
|---|---|
| 1% zinc gluconate | 2.5* |
| 0.6% zinc gluconate | 1.5 |
| 0.3% zinc gluconate | 1.0 |
| 1% zinc gluconate + 0.2% zinc acetate | 1.0 |
| 1% zinc gluconate + 0.2% zinc acetate + 0.2% zinc citrate | 0.5 |
| 1% zinc gluconate + 0.4% zinc acetate + 0.2% zinc citrate* | 0.2 |
| 0.4% zinc acetate + 0.2% zinc citrate | 0.5 |
| 0.5% zinc gluconate + 0.1% zinc acetate + 0.1% zinc citrate | 0.5 |
| 0.3% zinc lactate + 0.3% zinc acetate | 1.5 |
| 0.3% zinc gluconate + 0.2% zinc lactate + 0.2% zinc acetate | 0.5 |
| 0.3% zinc gluconate + 0.1% zinc acetate + 0.1% zinc lactate | 0.5 |
| Control (lubricant base only) | 3.0 |

*Burning sensation

Based on these findings, gels incorporating zinc gluconate alone were not able to prevent methyl salicylate-induced irritation, and in fact higher proportions of zinc gluconate may cause some burning sensation independent of the methyl salicylate irritant. In contrast, gels incorporating two or more of the zinc salts consisting of zinc gluconate, zinc acetate, zinc lactate and zinc citrate significantly reduced the irritant effects of methyl salicylate. One of these triple zinc salt compositions (1% zinc gluconate+0.4% zinc acetate+0.2% zinc citrate) reduced the redness induced by the methyl salicylate, but also produced some burning sensation in the volunteer. Interestingly, a gel formulation containing these same three zinc salts but at a lower concentration (0.5% zinc gluconate+0.1% zinc acetate+0.1% zinc citrate) was nearly as effective in preventing the methyl salicylate-induced irritation, but did not cause any burning.

5.3. Example

Evaluation of the Anti-Irritant Effect of Zinc Salt-Containing Lubricant Compositions on Nonoxynol-9-induced Irritation of Vaginal Mucosa in a Rabbit Model Nonoxynol-9, when present in gel-based lubricants at 9% w/w, has been shown to be a human irritant. Nonoxynol-9 has also been shown to produce irritation of the vaginal mucosa in a rabbit model. This animal model was used to evaluate the anti-irritant efficacy of various zinc salt compositions in vivo. Due to the limited number of animals available, only a limited number of zinc salt combinations could be tested. Because zinc gluconate has been shown to prevent latex allergies, this salt was tested alone and also in combination with zinc lactate and zinc acetate, which represented one of the better combinations of zinc salts identified in example 2 and still contained an amount of zinc gluconate sufficient to protect against allergic reactions to latex.

In these studies, three groups of rabbits containing six animals each received one of three treatments as indicated in Table 3. The zinc salts indicated in this table were mixed in a lubricant base (base composition was the same as in Example 1) which also contained the spermicidal agent nonoxynol-9 (9% w/w). Two ml of the zinc salt lubricant compositions indicated in Table 3 was instilled into the vagina of each rabbit daily for five consecutive days. At the end of this period, a veterinary pathologist evaluated each animal both macroscopically and microhistopathologically and scored the degree of vaginal irritation that was present. Irritation was quantified as follows: 0=No irritation, 1-4=Minimal Irritant, 5-8=Mild Irritation, 9-11=Moderate Irritation, 12-16=Severe Irritation. The veterinary pathologist indicated that a degree of irritation represented by a score of 3 or less would not be noticeable in humans, while a score of 8 or more would be associated with noticeable irritation in at least some human subjects.

As shown in Table 3, gel-based lubricant containing 9% nonoxynol-9 produces mild to moderate irritation of the vaginal mucosa in rabbits, and this irritation is actually exacerbated by the presence of zinc gluconate (0.3% w/w) alone. In contrast, when this same proportion of zinc gluconate is added together with zinc lactate and zinc acetate, each at 0.1% w/w, the irritating effects of nonoxynol-9 are largely prevented. These findings suggest that this triple zinc salt combination can be used to prevent irritation from spermicides and microbicides, and may also reduce latex-induced irritation when applied on the surface of a latex condom.

TABLE 3

Reduction of Nonoxynol-9-induced Vaginal Mucosal Irritation by Zinc

| Treatment Group | Salts Score (0-16) | | | | | | Average |
|---|---|---|---|---|---|---|---|
| 0.3% zinc gluconate | 2 | 16 | 6 | 16 | 7 | 16 | 10.5 |
| 0.3% zinc gluconate + 0.1% zinc lactate + 0.1% zinc acetate | 3 | 3 | 3 | 4 | 3 | 3 | 3 |
| Negative Control - lubricant base only | 16 | 7 | 7 | 6 | 7 | 6 | 8 |

5.4. Example 4

Evaluation of the Effects of Zinc Salts on the Detergent Actions of Nonoxynol-9

As introduced above, nonoxynol-9 is a spermicidal agent commonly used in genital lubricants. However, this agent is known to cause irritation and abrasions of the vaginal wall, creating the counter-productive risk of higher rates of infection by sexually-transmitted disease-causing pathogens including viruses or bacteria. Zinc salts can be incorporated into nonoxynol-9-containing lubricants to prevent this irritation, but they may also prevent the desired spermicidal effects of this compound. Thus, additional studies were performed to examined which zinc salts, and at what levels, could potentially interfere with the spermicidal effects of nonoxynol-9.

In these studies, the ability of nonoxynol-9 to lyse red blood cells was employed as an indirect indicator of its spermicidal effects. Thus, any composition of zinc salts that prevented the nonoxynol-9-mediated lysis of red blood cells would be likely to prevent the spermicidal effects of this compound and therefore be unsuitable as an anti-irritant in genital lubricants containing this spermicide. Lysis was evaluated be mixing 0.5 ml of a gel base formulation (60% propylene glycol, 40% water and 0.075% hydroxymethyl propyl cellulose (K-100M)) containing 8% nonoxynol-9 and the various combinations of zinc salts shown in Table 4 with 0.5 ml of red blood cells isolated from rats. After five minutes of incubation at 37° C., the mixtures were centrifuged and the resulting supernatants were examined for signs of red blood cell lysis. Lysis was scored as follows: +=100% lysis, ±=50% lysis, −=no lysis.

As shown in Table 4, zinc ion concentrations of 0.28% when introduced as zinc acetate impair the ability of nonoxynol-9 to lyse red blood cells. Interestingly, when the concentration of zinc ions is increased even further (to up to 0.38%) by the incorporation of both zinc gluconate and zinc acetate into the gel, the lytic activity of nonoxynol-9 is maintained. This finding further demonstrates the advantages of combinations of zinc salts over single zinc salts.

TABLE 4

Effect of Zinc Salts on the Detergent Actions of Nonoxynol-9

| Zinc Salt Formulation of Gel | Percentage of Zinc Ions | Lysis |
|---|---|---|
| Negative Control (lubricant base only) | — | − |
| Positive Control (lubricant base plus 8% nonoxynol-9) | | + |
| 0.8% zinc acetate | 0.28 | − |
| 0.4% zinc acetate | 0 14 | + |
| 2% zinc gluconate | 0.24 | + |
| 2% zinc gluconate + 0.4% zinc acetate | 0.24 + 0.14 (0.38) | + |
| 1% zinc gluconate + 0.4% zinc acetate | 0.12 + 0.14 (0.26) | + |
| 1% zinc gluconate + 0.2% zinc acetate | 0.12 + 0.07 (0.19) | + |
| 0.3% zinc gluconate + 0.2% zinc acetate + 0.2% zinc lactate | 0.045 + 0.07 + 0.05 (0.165) | + |
| 0.3% zinc gluconate + 0.2% zinc acetate + 0.2% zinc citrate | 0.045 + 0.07 + 0.00 (0.115) | + |

The above-described studies suggest that zinc salts may be added to nonoxynol-9-containing lubricants without impairing the detergent activities of the nonoxynol-9. However, the assay of nonoxynol-9-induced lysis employed in these studies was not quantitative. A second study was therefore performed to quantify the effects of the addition of zinc salts on the detergent action of nonoxynol-9.

In these studies, 0.5 ml of lubricant (0.5 ml of PBS in the case of control) is added to 0.5 ml of packed red blood cells. After a five minute incubation at mom temperature, the mixture is diluted with 1 ml PBS, mixed and centrifuged. The supernatant (containing the lysed red cells) is diluted 1:100 with PBS. Red cell hemolysis is then quantified by measuring the absorbance of 450 mm wavelength light transmitted by the lysed cell supernatant using a Spectronic-20 spectrophotometer. The high amount of absorbance indicates that a high amount of hemolysis has occurred. A solution containing only PBS is used as a blank reference.

The following two lubricants were compared:

| Lubricant 1 (Lubricant Base Only) | |
|---|---|
| Xanthum gum | 0.3% |
| Water | 44.1% |

-continued

| Lubricant 1 (Lubricant Base Only) | |
|---|---|
| Propylene Glycol | 55% |
| Silcone DC225 | 0.3% |
| Silicone CD1403 | 0.3% |

| Lubricant 2 (Lubricant Base plus Zinc Salts) | |
|---|---|
| Xanthum gum | 0.3% |
| Water | 43.6% |
| Zinc gluconate | 0.3% |
| Zinc acetate | 0.1% |
| Zinc lactate | 0.1% |
| Propylene Glycol | 60% |
| Silicone DC225 | 0.3% |
| Silicone DC1403 | 0.3% |

TABLE 5

Quantitation of the Effects of Zinc Salts on the Detergent Action of Nonoxynol-9

| Lubricant | Optical Density (O.D. 450) |
|---|---|
| Control (Red Cells + PBS) | 0.22 |
| Lubricant 1 + NN9 (9% w/w) | 0.50 |
| Lubricant 2 + NN9 (9% w/w) | 0.44 |

Although the addition of zinc salts to the lubricant base exerted a slight effect on the ability of nonoxynol-9 to lyse red blood cells, this effect was not statistically significant. Thus, the zinc salt composition containing 0.3% zinc gluconate+0.1% zinc acetate+0.1% zinc lactate does not interfere with the detergent action of NN9, and the same or lower concentrations of zinc salts can be used as an anti-irritant in sexual lubricants and creams of lubricants containing antimicrobial/antiviral agents which are used to prevent STD.

5.5. Example 5

Evaluation of the Effects of Zinc Salts on the Antimicrobial Action of Chlorhexidine Gluconate Chlorhexidine gluconate is a microbicidal agent commonly used in antiseptic gels and creams employed in wound dressing. However, this agent is known to cause irritation in at least some proportion of the human population. Zinc salts may be incorporated into chlorhexidine-containing products to prevent this irritation, but they may also prevent the desired microbicidal effects of this compound. Thus, a series of studies were initiated to examine whether zinc salts interfered with the microbicidal effects of chlorhexidine.

In these studies, the ability of chlorhexidine to inhibit the growth of S. aureus in culture was employed as an indicator of chlorhexidine's microbicidal effects. Briefly, 0.5 ml of a solution containing 1% chlorhexidine gluconate (CHG), 50% ethanol and 50% propylene glycol, plus or minus 2% zinc gluconate, was spread on the surface of a 3 cm×3 cm piece of wound dressing. After drying for one hr, the dressing was subdivided into 1 cm×1 cm pieces and placed on the surface of a Trypticase Soya Agar (TSA) plate seeded with 0.3 ml of S. aureus ($10^8$ colony-forming units (cfu)/ml). The plates were incubated at 37° C. for 24 hr and the zone of inhibition was measured. The results of these studies are shown below in Table 5. The addition of 2% zinc gluconate had no effect on the ability of chlorhexidine to inhibit the growth of S. aureus, indicating that the addition of this concentration of zinc to a gel containing this microbicidal agent did not result in its inactivation.

TABLE 6

Effect of Zinc on the Microbicidal Action of Chlorhexidine

| Treatment | Zone of inhibition (mm) |
|---|---|
| Blank (no solution) | 0 |
| Negative Control (CHG solution without zinc) | 14 |
| CHG solution + 2% zinc gluconate | 17 |

5.6. Example 6

Hydroalcoholic Gel Formulations Containing Zinc Salt Complexes

The following alcohol gel formulations containing anti-irritant zinc salt complexes were prepared and some were then evaluated for their rapid and sustained disinfectant activity either in vitro or in two volunteers who have shown irritation and redness following exposure to certain alcohol gels (Prevacare™, Johnson & Johnson).

| | (% By weight) |
|---|---|
| ZINC GEL A | |
| Water | 26.63 |
| Ucare (JR 30) | 0.3 |
| Zinc gluconate | 0.3 |
| Zine acetate | 0.1 |
| Zinc lactate | 0.1 |
| Germall plus | 0.2 |
| Chlorhexidine gluconate | 0.05 |
| Benzalkonium chloride | 0.12 |
| Ethanol | 70 |
| Phenoxyethanol | 0.7 |
| Glycerin | 1.0 |
| Cetyl ether (PPG 10) | 0.5 |
| ZINC GEL B | |
| Water | 26.13 |
| Ucare (JR 30) | 0.3 |
| Zinc gluconate | 0.3 |
| Zinc acetate | 0.1 |
| Zinc lactate | 0.1 |
| Germall plus | 0.2 |
| Chlorhexidine gluconate | 0.05 |
| Benzalkonium chloride | 0.12 |
| Ethanol | 76 |
| Phenoxyethanol | 0.7 |
| Glycerin | 1.0 |
| Cetyl ether (PPG 10) | 0.5 |
| Vitamin C | 0.5 |
| ZINC GEL C | |
| Water | 25.53 |
| Ucare (JR 30) | 0.3 |
| Zinc gluconate | 0.3 |
| Zinc acetate | 0.1 |
| Zinc lactate | 0.1 |
| Germall plus | 0.2 |
| Chlorhexidine gluconate | 0.05 |
| Benzalkonium chloride | 0.12 |
| Ethanol | 70 |
| Klucel | 0.3 |
| Phenoxyethanol | 0.7 |
| Glycerin | 1.0 |
| Cetyl ether (PPG 10) | 0.5 |
| Triclosan | 0.3 |
| Vitamin C (Ascorbic acid) | 0.5 |

-continued

| | (% By weight) |
|---|---|
| ZINC GEL D | |
| Water | 26.13 |
| Ucare (JR-30) | 0.2 |
| Zinc gluconate | 0.3 |
| Zinc acetate | 0.1 |
| Zinc lactate | 0.1 |
| Germall plus | 0.2 |
| Chlorhexidine gluconate | 0.05 |
| Benzalkonium chloride | 0.12 |
| Ethanol | 70 |
| Incroquat | 0.6 |
| Phenoxyethanol | 0.7 |
| Glycerin | 1.0 |
| Cetyl ether (PPG 10) | 0.5 |
| ZINC GEL D1 | |
| Water | 26.73 |
| Ucare (JR-30) | 0.2 |
| Zinc gluconate | 0.3 |
| Zinc acetate | 0.1 |
| Zinc lactate | 0.1 |
| Germall plus | 0.2 |
| Chlorhexidine gluconate | 0.05 |
| Benzalkonium chloride | 0.12 |
| Ethanol | 70 |
| Phenoxyethanol | 0.7 |
| Glycerin | 1.0 |
| Cetyl ether (PPG 10) | 0.5 |
| ZINC GEL E | |
| Water | 25.33 |
| Ucare (JR 30) | 0.2 |
| Zinc gluconate | 0.3 |
| Zinc acetate | 0.1 |
| Zinc lactate | 0.1 |
| Germall plus | 0.2 |
| Chlorhexidine gluconate | 0.05 |
| Benzalkonium chloride | 0.12 |
| Ethanol | 70 |
| Incroquat | 0.6 |
| Phenoxyethanol | 0.7 |
| Glycerin | 1.0 |
| Cetyl ether (PPG10) | 0.5 |
| Triclosan | 0.3 |
| Vitamin C | 0.5 |
| ZINC GEL F | |
| Water | 26.08 |
| Ucare (JR30) | 0.2 |
| Zinc gluconate | 0.1 |
| Zinc acetate | 0.1 |
| Zinc lactate | 0.05 |
| Germall plus | 0.2 |
| Chlorhexidine gluconate | 0.05 |
| Benzalkonium chloride | 0.12 |
| Ethanol | 70 |
| Incroquat | 0.6 |
| Phenoxyethanol | 0.7 |
| Glycerin | 1.0 |
| Cetyl ethyl (PPG10) | 0.5 |
| Incromide CAC | 0.3 |
| ZINC GEL G | |
| Water | 26.55 |
| Ucare (JR30) | 0.2 |
| Zinc gluconate | 0.1 |
| Zinc acetate | 0.1 |
| Zinc lactate | 0.05 |
| Germall plus | 0.2 |
| Ethanol | 70 |
| Incroquat | 0.6 |
| Phenoxyethanol | 0.7 |
| Glycerin | 1.0 |
| Cetyl ethyl (PPG10) | 0.5 |

Rapidity Of Action In Vitro. To test for rapid activity, 0.2 ml of $10^9$ cfu/ml of bacterial culture or $10^6$ cfu/ml of fungal culture (diluted 1:1 with bovine adult serum) was placed in a sterile culture tube and 0.8 ml of the zinc gel was added and mixed. After 15 seconds, the antimicrobial activity was stopped with LTSB (Lecithin-containing Trypticase Soya Broth; a drug-inactivating media) and an aliquot was subcultured on a TSA (Trypticase Soya Agar) plate. The plates were then incubated for 24 hours at 37° C. to determine the number of microbial colonies per tube. Phosphate buffered saline was used instead of gel for the control. As shown in Table 7, no active bacteria or fungi could be recovered from any of the tubes 15 seconds after the addition of zinc gels A, D and G. In contrast, nearly all of the bacteria or fungi could be recovered from the tubes to which PBS was added.

TABLE 7

The Rapid Disinfectant Actions of Hydroalcoholic Gels Containing Zinc Salts

| Organism | Zinc Gel A (cfu/tube) | Zinc Gel D (cfu/tube) | Zinc Gel G (cfu/tube) | Control (cfu/tube) |
|---|---|---|---|---|
| *S. aureus* | 0 | 0 | 0 | $1.1 \times 10^7$ |
| *S. epidermis* | 0 | 0 | 0 | $1.0 \times 10^7$ |
| *S. aureus* (methicillin resistant) | 0 | 0 | 0 | $7.3 \times 10^6$ |
| *K. pneumoniae* | 0 | 0 | 0 | $3.0 \times 10^7$ |
| *E. coli* | 0 | 0 | 0 | $2.3 \times 10^6$ |
| *C. albicans* | 0 | 0 | 0 | $1.5 \times 10^5$ |

Sustainability of Disinfectant Action In Vitro. Hides from freshly killed pigs were obtained front a slaughter house. The skin was washed with water, dehaired and defatted using scalpel. It was then cut into smaller sections, rinsed with water and preserved in sealed plastic bags in a freezer. Before use, a section was removed, thawed and rinsed in water and cut into pieces (3×3 cm) with a blade. These skin pieces were mounted on holders (plastic plates of 5 cm diameter) with epoxy to expose the skin surface. Two pieces of skin were used per sample. 0.3 ml of the test formulation was applied on one piece and rubbed on other piece from a matched pair for 30 sec. After 15 min, one of the two pieces was inoculated with 30 μl of a S. aureus culture ($10^7$ cfu/ml). The two matching skin pieces were rubbed together for 15 sec. After 30 sec, each skin piece was rinsed with LTSB to recover viable organisms and an aliquot from this LTSB wash was subcultured on a D/E plate to quantitate the surviving organisms. Zinc gel without any antiseptic was used as control. As shown in Table 8, Prevacare™ and Avagard™ killed approximately 50% and 90%, respectively, of the bacteria inoculated on the pig skin 15 minutes after their application. In contrast, more than 99.9% of all inoculated bacteria were killed when applied to pig skin 15 minutes after treatment with Zinc gels D or E. These findings indicate that these zinc gels retain their full potency as disinfectants for at least 15 minutes after their use, and therefore are superior to the existing hydroalcoholic gel disinfectants Prevacare™ and Avagard™.

TABLE 8

The Sustainability of the Disinfectant Actions of Hydroalcoholic Gels Containing Zinc Salts

| Formulation | cfu/test |
|---|---|
| Control | $3.0 \times 10^5$ |
| Zinc Gel D | 48 |
| Zinc Gel E | 3 |
| Prevacare ™ | $1.5 \times 10^5$ |
| Avagard ™ | $3.9 \times 10^4$ |

Hydroalcoholic Zinc Gels Fail to Irritate the Skin of Individuals Sensitive to Other Hydroalcoholic Gels. Two volunteers who had previously exhibited sensitivity to the hydroalcoholic gel Prevacare™ were enlisted for this study. Two gm of Prevacare™ or the zinc gel indicated in Table 9 was applied to the palm and spread all over the hands. Skin reactions were observed after 15 minutes of exposure to the gel. The results of these studies are shown in Table 9.

TABLE 9

Hydroalcoholic Zinc Gels Are Not Irritating To individuals Who Exhibit Sensitivity to Prevacare ™.

| Volunteer | Prevacare ™ | Zinc Gel A | Zinc Gel E |
|---|---|---|---|
| 1 | Redness | None | None |
| 2 | Redness and Itching | None | None |

In an unrelated study of the antimicrobial efficacy of Avagard™, it was also noted that this hydroalcoholic gel also caused skin irritation in some individuals. Thus, the above findings may be of general significance to the prevention of skin irritation induced by alcohol-based disinfectant products.

5.7. Example 7

Evaluation of the Effects of Zinc Salts on the Prevention of Latex-induced Contact Dermatitis Latex gloves are known to cause contact dermatitis in some individuals. Latex-induced contact dermatitis is an especially serious concern among surgeons and other health care workers who face unavoidable exposure to latex in surgical gloves and other medical devices. The following three zinc gel surgical hand preps may be useful in protecting against this problem.

| | (% by wt) |
|---|---|
| ZINC GEL SURGICAL HAND PREP-1 | |
| Water | 33.13 |
| Ucare (JR30) | 0.2 |
| Zinc gluconate | 0.5 |
| Zinc acetate | 0.1 |
| Zinc lactate | 0.1 |
| Germall plus | 0.2 |
| Chlorhexidine gluconate | 0.05 |
| Benzalkonium chloride | 0.12 |
| Ethanol | 60 |
| Incroquat | 0.6 |
| Polawax | 0.5 |
| Zinc stearate | 2.0 |
| Phenoxyethanol | 0.7 |
| Glycerin | 1.0 |
| Cetyl ether (PPG10) | 0.5 |
| Silicone DC1403 | 0.3 |
| ZINC GEL SURGICAL HAND PREP-2 | |
| Water | 30.03 |
| Ucare (JR30) | 0.2 |
| Zinc gluconate | 0.5 |
| Zinc acetate | 0.1 |
| Zinc lactate | 0.1 |
| Germall plus | 0.2 |
| Chlorhexidine gluconate | 0.05 |
| Benzalkonium chloride | 0.12 |
| Ethanol | 63 |
| Incroquat TMS | 0.6 |
| Polawax | 0.3 |
| Stearyl alcohol | 0.3 |

-continued

| | (% by wt) |
|---|---|
| Zinc stearate | 2.0 |
| Phenoxyethanol | 0.7 |
| Glycerin | 1.0 |
| Cetyl ether (PPG10) | 0.5 |
| Silicone DC1403 | 0.3 |
| ZINC GEL SURGICAL HAND PREP-3 | |
| Water | 29.13 |
| Ucare (JR30) | 0.2 |
| Zinc gluconate | 0.5 |
| Zinc acetate | 0.1 |
| Zinc lactate | 0.1 |
| Germall plus | 0.2 |
| Chlorhexidine gluconate | 0.05 |
| Benzalkonium chloride | 0.12 |
| Ethanol | 65 |
| Incroquat | 0.6 |
| Polawax | 0.5 |
| Zinc stearate | 1.0 |
| Phenoxyethanol | 0.7 |
| Glycerin | 1.0 |
| Cetyl ether (PPG10) | 0.5 |
| Silicone DC1403 | 0.3 |

The efficacy of zinc gel surgical hand prep-1 was tested on a volunteer known to develop contact dermatitis when in contact with latex gloves. In this study, the volunteer donned latex gloves and carried out normal activities. After 30 min, redness and irritation was observed on the back or the palm of the hand. Later that same day, after the redness and irritation subsided, the volunteer applied 2 g of the zinc surgical hand prep and, after the alcohol evaporated off, donned latex gloves. No reaction was seen when the gloves were removed after 2 hours. These findings confirm the potential utility of zinc-containing gels to prevent latex-induced contact dermatitis.

5.8. Example 8

The Incorporation of Zinc Salts into Alcohol Gel Wipes Prevents the Irritating Effects of Alcohol While Maintaining Disinfectant Efficacy Individually sealed alcohol-impregnated wipes are useful for the disinfection of topical and various other physical surfaces. When applied topically, however, the alcohol from the wipe may sometimes cause skin irritation. Thus, the addition of zinc salt formulations to alcohol gel wipes is useful in preventing alcohol-induced skin irritation. One such zinc-containing alcohol gel wipe for hand disinfection is composed of the following:

| ZINC GEL X SOLUTION | (% By weight) |
|---|---|
| Water | 20.93 |
| Ucare (JR 30) | 0.2 |
| Zinc gluconate | 0.3 |
| Zinc acetate | 0.1 |
| Zinc lactate | 0.1 |
| Germall plus | 0.2 |
| Chlorhexidine gluconate | 0.05 |
| Benzalkonium chloride | 0.12 |
| Ethanol | 75 |
| Incroquat | 0.6 |
| Polawax | 0.2 |
| Phenoxyethahol | 0.7 |
| Glycerin | 1.0 |
| Cetyl ether (PPG 10) | 0.5 |

Five ml of this solution is dispensed onto each wipe and the wipes are packed in plastic lined bags and sealed for future use as aids in disinfection.

5.9. Example 9

The incorporation of Zinc Salts into Gels and Creams to Potentiate Their Anti-itch Properties Various gels and creams are known in the art for their abilities to treat itchiness or psoriasis. However, some of the ingredients contained in these products may in fact cause irritation in the very individuals they are intended to treat. The incorporation of zinc salt formulations to these products will prevent their irritating properties while retaining their therapeutic effects.

A triple zinc anti-itch aqueous cream or lotion is composed of the following:

| TRIPLE ZINC ANTI-ITCH LOTION | (% by wt) |
|---|---|
| Incroquat TMS | 0.8 |
| Polawax NF | 0.8 |
| Petroleum Jelly | 3.0 |
| Crothix | 1.0 |
| Crodomol MM | 1.0 |
| Cremerol | 1.0 |
| Propylene glycol | 2.0 |
| Glycerin | 8.0 |
| Water | 77.3 |
| Ucare JR30 | 0.2 |
| Germall plus | 0.2 |
| Zinc gluconate | 1.0 |
| Zinc acetate | 0.1 |
| Zinc lactate | 0.1 |
| Zinc stearate | 3.0 |
| Zinc oxide | 0.5 |

A triple zinc cream for the treatment of psoriasis is composed of the following:

| TRIPLE ZINC CREAM FOR TREATING PSORIASIS | (% by wt) |
|---|---|
| Petroleum Jelly | 25 |
| Incroquat | 1.0 |
| Polawax NF | 1.0 |
| Glycerin | 10.0 |
| Propylene Glycol | 10.0 |
| Crothix | 2.0 |
| Zinc oxide | 3.0 |
| Zinc stearate | 3.0 |
| Allatoin | 0.5 |
| Salicylic acid | 2.0 |
| Dimethicone | 2.0 |
| Water | 38.8 |
| Zinc gluconate | 1.0 |
| Zinc acetate | 0.1 |
| Zinc lactate | 0.1 |
| Germall plus | 0.2 |
| Chlorhexidine gluconate | 0.05 |
| Benzalkonium chloride | 0.05 |
| Ucare JR 30 | 0.2 |

To treat itchiness or psoriasis, a therapeutically effective amount of the triple zinc anti-itch lotion or the triple zinc cream for treating psoriasis is applied to the area to be treated as necessary to maintain the skin surface free or itchiness or the symptoms of psoriasis.

5.10. Example 10

The Incorporation of Zinc Salts into Anti-microbial Gels Containing Chlorhexidine Gluconate and Benzalkonium Chloride Does Not Reduce Their Anti-microbial Efficacy The antimicrobial agents chlorhexidine gluconate and benzalkonium chloride are known in the art as preservatives in various products. What was not previously appreciated in the art, however, was that the addition of incroquat significantly potentiates the preservative effects of chlorhexidine gluconate and benzalkonium chloride. To demonstrate this synergism between incroquat and chlorhexidine gluconate and benzalkonium chloride, gels with or without chlorhexidine gluconate and benzalkonium chloride or with or without incroquat were examined for the rapidity with which they could kill bacteria in culture. In these studies, 1 ml of $10^8$ cfu of S. aureus was mixed with 1.0 ml of Bovine Adult Serum (BAS) and 1.0 ml of the one of the gels indicated below in Table 10. After 15 seconds, a 0.5 ml aliquot was removed and added to 4.5 ml of the drug inactivating media LTSB. The resulting mixture was then diluted 100 fold with LTSB. After mixing, a 0.5 ml aliquot of the diluent was plated on TSA plates, which then were incubated at 37° C. for 24 hours to determine the colony counts.

TABLE 10

Compositions of Gels Containing Various Combinations of Chlorhexidine Gluconate and Benzalkonium Chloride and Incroquat.

| Ingredients | Gel # 1 | Gel # 2 | Gel # 3 | Gel # 4 | Gel # 5 | Gel # 6 |
|---|---|---|---|---|---|---|
| Water | 33.3 | 33.125 | 33.0 | 32.825 | 32.525 | 32.25 |
| U care (JR30) | 0.2 | 0.2 | 0.2 | 0.2 | 0.2 | 0.2 |
| Ethanol | 65 | 65 | 65 | 65 | 65 | 65 |
| Glycerin | 1.0 | 1.0 | 1.0 | 1.0 | 1.0 | 1.0 |
| Cetylether PPG10) | 0.5 | 0.5 | 0.5 | 0.5 | 0.5 | 0.5 |
| CHG | — | 0.05 | — | 0.05 | 0.05 | 0.05 |
| BZK | — | 0.125 | — | 0.125 | 0.125 | 0.125 |
| Incroquat | — | — | 0.3 | 0.3 | 0.6 | 0.6 |
| Zinc gluconate | | | | | | 0.15 |
| Zinc acetate | — | — | — | — | — | 0.1 |
| Zinc lactate | — | — | — | — | — | 0.05 |

As shown in Table 11, the addition of chlorhexidine gluconate and benzalkonium chloride to the gel base (Gel #2) resulted in a ten-fold reduction in the amount of bacteria recovered over that observed with the gel base alone. The addition of incroquat alone to the gel base (Gel #3) only mildly affected the numbers of bacteria that could be recovered at 24 hrs after the addition of the gel to the bacterial culture. However, the addition of chlorhexidine gluconate, benzalkonium chloride and incroquat to the gel base (Gel #4) resulted in a 4-log reduction in the amount of bacteria that could be recovered from the culture. Thus, there is a high degree of synergy between the antibacterial effects of chlorhexidine gluconate and benzalkonium chloride and incroquat.

TABLE 11

The Addition of Incroquat Synergistically Potentiates the Anti-microbial Effects of Gels Containing Chlorhexidine Gluconate and Benzalkonium Chloride

| Gel | Bacterial Growth (cfu/tube) | Fold reduction over control |
|---|---|---|
| 1 | $3.0 \times 10^7$ | — |
| 2 | $3.0 \times 10^6$ | 1.0 |
| 3 | $1.6 \times 10^7$ | 0.48 |
| 4 | $3.0 \times 10^3$ | 4.0 |

Having established the strong synergy between chlorhexidine gluconate, benzalkonium chloride and incroquat, it was important to determine whether the further addition of potentially non-irritating zinc salts to this gel would abolish the anti-microbial effects. Thus, the consequences of the addition of zinc salts to gels with chlorhexidine gluconate, benzalkonium chloride and incroquat on their sustained anti-bacterial activity were evaluated using the pig skin model described above in Section 5.6. The results of these studies, shown in Table 12, demonstrate that the addition of zinc (Gel #6) did not interfere with the strong anti-microbial effect seen in gels containing chlorhexidine gluconate, benzalkonium chloride and incroquat (Gel #5) over those seen in gels containing only chlorhexidine gluconate and benzalkonium chloride (Gel #2) or the gel base alone (Gel #1). Thus, zinc salts may be added to anti-microbial gels containing chlorhexidine gluconate, benzalkonium chloride and incroquat to prevent their potential irritation without compromising their anti-microbial effects.

TABLE 12

The Anti-microbial Synergism Observed in Gels Containing Chlorhexidine Gluconate, Benzalkonium Chloride and Incroquat is Maintained in the Presence of Zinc Salts

| Gel Formulation | Bacterial Growth (cfu/test) |
|---|---|
| Gel #1 | $1.8 \times 10^5$ |
| Gel #2 | $4.1 \times 10^4$ |
| Gel #5 | $2.0 \times 10^2$ |
| Gel #6 | $1.0 \times 10^2$ |

This finding of synergistic anti-microbial activity between chlorhexidine gluconate, benzalkonium chloride and incroquat in the presence of zinc salts was also observed in alcohol-based gels. For example, as shown in Table 13, a 4-log reduction in bacterial growth was observed in an alcohol-based zinc hydrogel containing chlorhexidine gluconate, benzalkonium chloride and incroquat (gel D; see Section 5.6), as compared to the only 2-log reduction in bacterial growth observed with zinc gel D1 (see Section 5.6), which containing chlorhexidine gluconate and benzalkonium chloride but lacked incroquat. These findings confirm that the addition of incroquat significantly potentiates the preservative effects of chlorhexidine gluconate and benzalkonium chloride, and that these preservative effects are not abolished by the presence of zinc salts within the gel.

TABLE 13

The Addition of Incroquat Potentiates the Anti-microbial Effects of Zinc Gels Containing Chlorhexidine Gluconate and Benzalkonium Chloride

| Gel Formulation | Bacterial Growth (cfu/test) |
|---|---|
| Control Base* | $4.0 \times 10^5$ |
| Zinc Gel D1 | $2.0 \times 10^3$ |

TABLE 13-continued

The Addition of Incroquat Potentiates the Anti-microbial Effects of Zinc Gels Containing Chlorhexidine Gluconate and Benzalkonium Chloride

| Gel Formulation | Bacterial Growth (cfu/test) |
|---|---|
| Zinc Gel D | $1 \times 10^2$ |
| Prevacare | $1.5 \times 10^5$ |

*Control bae is same as D1 except does not contain Germallplus, chlorhexidine gluconate, benzalkonium chloride and phenoxyethenol.

Synergistic potentiation of anti-microbial activity is also observed in gels containing chlorhexidine gluconate, benzalkonium chloride, incroquat and sensiva (octoxyglycerin). Thus, additional studies were performed to establish that the synergistic anti-microbial effects of these compounds was not abolished by the addition of zinc salts to gels containing these ingredients. The compositions of the gels tested are shown in Table 14. The studies were performed using the pig skin model described above in Section 5.6. As shown in Table 15, the addition of zinc (Gel #3) did not interfere with the strong anti-microbial effect seen in gels containing chlorhexidine gluconate, benzalkonium chloride, incroquat and sensiva (Gel #2) over those seen in gels containing only sensiva (Gel #5), incroquat (Gel #4), sensiva plus incroquat (Gel #6), chlorhexidine gluconate, benzalkonium chloride, and sensiva (Gel #1) or the gel base alone (Gel #7). Thus, zinc salts may be added to anti-microbial gels containing chlorhexidine gluconate, benzalkonium chloride, incroquat and sensiva to prevent their potential irritation without compromising their anti-microbial effects.

TABLE 14

Compositions of Gels Containing Various Combinations of Chlorhexidine Gluconate, Benzalkonium Chloride, y Incroquat and Sensivag

| Ingredients | Gel # 1 | Gel # 2 | Gel # 3 | Gel # 4 | Gel # 5 | Gel # 6 | Gel # 7 |
|---|---|---|---|---|---|---|---|
| Water | 32.125 | 31.525 | 31.225 | 32.7 | 32.3 | 32.9 | 33.3 |
| Ucare | 0.2 | 0.2 | 0.2 | 0.2 | 0.2 | 0.2 | 0.2 |
| Ethanol | 65 | 65 | 65 | 65 | 65 | 65 | 65 |
| Glycerin | 1.0 | 1.0 | 1.0 | 1.0 | 1.0 | 1.0 | 1.0 |
| Cetylether PPG10 | 0.5 | 0.5 | 0.5 | 0.5 | 0.5 | 0.5 | 0.5 |
| CHG | 0.05 | 0.05 | 0.05 | — | — | — | — |
| BZK | 0.125 | 0.125 | 0.125 | — | — | — | — |
| Sensiva | 1.0 | 1.0 | 1.0 | | 1.0 | 1.0 | |
| Incroquat | — | 0.6 | 0.6 | 0.6 | — | 0.6 | — |
| Zinc gluconate | — | — | 0.15 | — | — | — | — |
| Zinc acetate | — | — | 0.1 | — | — | — | — |
| Zinc lactate | — | — | 0.05 | — | — | — | — |

TABLE 15

The Anti-microbial Synergism Observed in Gels Containing Chlorhexidine Gluconate, Benzalkonium Chloride, Incroquat and Sensiva is Maintained in the Presence of Zinc Salts

| Gel Formulation | Bacterial Growth (cfu/test) |
|---|---|
| Gel #1 | $7.9 \times 10^2$ |
| Gel #2 | $3.0 \times 10^1$ |
| Gel #3 | $2.0 \times 10^1$ |
| Gel #4 | $1.6 \times 10^5$ |
| Gel #5 | $2.9 \times 10^4$ |
| Gel #6 | $3.0 \times 10^3$ |
| Gel #7 | $3.0 \times 10^5$ |

5.11. Example 11

The Incorporation of Zinc Salts into Hydroalcoholic Gels Containing 1.0% Chlorhexidine Prevents the Irritating Effects of Alcohol and Chlorhexidine While Maintaining Disinfectant Efficacy Latex gloves are beneficial in minimizing or preventing transmission of various infectious agents, but an increasing proportion of the population is developing an allergic reaction to latex that results in the development of contact dermatitis. Because zinc salts can prevent the irritation caused by latex, the addition of zinc salts to hydroalcoholic gels or creams to be applied to the skin underneath the glove will be useful in preventing this latex-induced contact dermatitis. Furthermore, if the hydroalcoholic gels also comprise 1.0% chlorhexidine, the barrier to the transmission of infectious agents will be further improved provided that the zinc salts do not inactivate the anti-microbial effects of the chlorhexidine. The following formulation therefore will be useful as a topical disinfectant to be applied to skin subsequently covered by latex articles.

| HYDROALCOHOLIC ZINC GEL CONTAINING 1.0% CHLORHEXIDINE FOR LONG TERM ACTIVITY | (% by wt) |
|---|---|
| Water | 25.25 |
| Ucare (JR 30) | 0.15 |
| Hydroxypropylmethylcellulose (K-100) | 0.15 |
| Germall plus | 0.2 |
| Zinc gluconate | 1.0 |
| Zinc acetate | 0.2 |
| Zinc lactate | 0.1 |
| Chlorhexidine gluconate (20%) | 5.0 |
| Benzalkonium chloride (50%) | 0.25 |
| Ethanol | 60 |
| Incroquat | 0.7 |
| Polawax | 0.3 |
| Phenoxyethahol | 0.7 |
| Glycerin | 2.0 |
| Cetylether (PPG 10) | 1.0 |
| Vitamin E | 0.2 |
| Zinc stearate | 3.0 |

The efficacy of the gel described immediately above was tested on a volunteer known to develop contact dermatitis when in contact with latex gloves. In this study, the volunteer applied 2 g of the hydroalcoholic zinc gel containing 1.0% chlorhexidine and, after the alcohol evaporated off, donned latex gloves and carried out normal activities. No reaction was seen when the gloves were removed after 3 hours. These findings confirm the potential utility of zinc-containing gels to prevent latex-induced contact dermatitis.

5.12. Example 12

Topical Creams Containing Triple Zinc Salts Protect Against Dermal Irritation Caused by Various Physical, Chemical, Mechanical or Biological Irritants A topical triple zinc anti-itch cream or lotion of the following composition was prepared:

| TRIPLE ZINC ANTI-ITCH LOTION | (% by wt) |
|---|---|
| Incroquat TMS Behenyl | 0.8 |
| Polawax NF | 0.8 |

-continued

| TRIPLE ZINC ANTI-ITCH LOTION | (% by wt) |
|---|---|
| Petroleum Jelly | 3.0 |
| Crothix | 1.0 |
| Crodomol MM | 1.0 |
| Cremerol HMG | 1.0 |
| Propylene glycol | 2.0 |
| Glycerin | 8.0 |
| Water | 77.3 |
| UCare JR30-M | 0.2 |
| Germall plus | 0.2 |
| Zinc gluconate | 0.3 |
| Zinc acetate | 0.1 |
| Zinc lactate | 0.1 |
| Zinc stearate | 3.0 |
| Zinc oxide | 0.5 |

The topical triple zinc anti-itch lotion then was tested on volunteers to determine whether it could protect against the skin irritation resulting from dryness (e.g. winter itch), prickly heat, mechanical insult (e.g. shaving or abrasive procedures), contact with poison ivy, diaper rash, contact with detergents such as sodium lauryl sulfate, nonoxinol-9, chemical agents, antimicrobial agents, alcohol, etc. The results of these studies are described in Table 16.

TABLE 16

Evaluation of Topical Triple Zinc Anti-itch Lotion in Prevention of Skin Irritation Caused by Physical, Chemical, Mechanical or Biological Irritants

| Problem/ Irritant | Number of volunteers tested | Time after application required for cessation of irritation/wound healing |
|---|---|---|
| Winter itch* | 4 | 10-15 minutes |
| Prickly heat | 1 | 15-20 minutes |
| Skin irritation after shaving | 2 | 5-10 minutes |
| Poison ivy | 2 | 10-15 minutes |
| psoriasis itch | 2 | 10-20 minutes |
| scratch wound | 1 | 2 days |

*Two of the four volunteers tried the same lotion without zinc gluconate, zinc acetate and zinc lactate, but the irritation ceased only after several applications.

Based on these observations, this triple zinc anti-itch lotion reduces the skin irritation produced by a wide range of irritants, including those of physical, chemical, biological, or mechanical origins.

5.13. Example 13

Topical Creams Containing Triple Zinc Salts Protect Against Dermal Irritation Caused by Essential Oils (EO) and Fragrance and Flavor (FF) Chemicals Essential oils are volatile oils obtained from plant or animal sources and are composed of complex mixtures of several constituents as monoterpenes and sesquiterpene hydrocarbons, monoterpene and sesquiterpene alcohols, esters, ethers, aldehydes, ketones, oxides and the like. These essential oils and their isolated constituents have been mainly used as fragrance and flavor agents in several formulations. These essential oils have also been known to show antimicrobial, anti-inflammatory and wound-healing properties.

However, there have been several reports about the skin-sensitizing effect of these essential oils. The spectrum of reported skin reactions to essential oils includes contact dermatitis, irritant contact dermatitis, phototoxic reactions and urticaria. See De Groot A, Frusch P J. Adverse reactions to fragrances: a clinical review. Contact Dermatitis 1997; 36:57-86. A mixture of almond, ylang-ylang, neroli, sandalwood and frankincense oils was shown to have resulted in a positive patch-test on a patient whose skin was exposed to the mixture of these oils. See Bleasel N, Tate B and Rademaker M. Allergic contact dermatitis following exposure to essential oils. Australian Journal of Dermatology 2002; 43:211-213. Repeated intradermal dosing with peppermint oil was reported to have produced moderate and severe reactions in rabbits. See Nair B. Final report on the safety assessment of Mentha Piperita (Peppermint) oil, Mentha Piperita (Peppermint) Leaf extract, Mentha Piperita (Peppermint) leaf and Mentha Piperita (Peppermint) water. International Journal of Toxicology 2001; 20 (Suppl 3):61-73.

Researchers have also shown that lavender oil is responsible for contact dermatitis using the patch testing method, which was carried out for a period of 9 years. See Sugiura M, Hayakawa R, Kato Y, Sugiura K, Hashimoto R. Results of patch testing with lavender oils in Japan, Contact Dermatitis 2000; 43:157-160. Jasmine absolute, geranium oil bourbon, spearmint oil, clove oil, lemongrass oil and cedarwood oil also have been shown to produce allergic contact dermatitis. See generally Larsen W, Nakayama H, Fischer T, Elsner P, Frosch P, Burrows D, Jordan W, Shaw S, Wilkinson J, Marks J Jr, Sugawara M, Nethercott M, Nethercott J. Fragrance contact dermatitis: a worldwide multicenter investigation (Part II). Contact Dermatitis 2001; 44:344-346; and Wohrl S, Hemmer W, Focke M. Gotz M. Jarisch R. The significance of fragrance mix, balsam of Peru, colophony and propolis as screening tools in the detection of fragrance allergy. British Journal of Dermatology 2001; 145(2):268-273. There has been a recent report that a girl who was using a fragrance containing the essential oil of tangerine, suffered from itching erythema and papules on areas of contact on the hands, face and neck. See Vilaplana J, Romaguera C. Contact dermatitis from the essential oil of tangerine in fragrances. Contact Dermatitis 2002; 46:108.

Apart from the essential oils, their individual ingredients, either isolated from the oil or chemically synthesized—have also been show to have skin sensitizing effect. L-citronellol, α-amylcinnamaldehyde and lyral have been shown to test positive to skin sensitization tests. See Larsen W, Nakayama H, Fischer T, Elsner P, Frosch P, Burrows D, Jordan W, Shaw S, Wilkinson J, Marks J Jr, Sugawara M, Nethercott M, Nethercott J. Fragrance contact dermatitis: a worldwide multicenter investigation (Part II). Contact Dermatitis 2001; 44:344-346. Geraniol, famesol, hydroxycitronellal, isoeugenol, and eugenol have also been reported to test positive to skin patch-tests See Larsen W, Nakayama H, Fischer T, Elsner P, Frosch P, Burrows D, Jordan W, Shaw S, Wilkinson J, Marks J Jr, Sugawara M, Nethercott M, Nethercott J. Fragrance contact dermatitis: a worldwide multicenter investigation (Part II). Contact Dermatitis 2001: 44:344-346 and Wohrl S, Hemmer W, Focke M, Gotz M, Jarisch R. The significance of fragrance mix, balsam of Peru, colophony and propolis as screening tools in the detection of fragrance allergy. British Journal of Dermatology 2001; 145(2):268-273. Eucalyptol was shown to result in the appearance of pruritus and erythema on the skin of an athlete, who was using a cream containing eucalyptol. See Vilaplana J, Romaguera C. Contact dermatitis from the essential oil of tangerine in fragrances. Contact Dermatitis 2002; 46:108.

In order to incorporate essential oils, their isolated ingredients and other natural or synthetic fragrance and flavor chemicals in topical formulations without causing contact dermatitis, the following topical formulations containing the triple zinc salts with and without essential oils (EO) and fragrance and flavor chemicals (FF) were prepared in aqueous and alcohol base:

Alcohol Zinc Gel Hand Wash #1

| Ingredient | % by weight |
|---|---|
| UCare JR30-M | 0.05 |
| Methocel K100 | 0.1 |
| Water | 36.08 |
| Zinc gluconate | 0.3 |
| Zinc acetate | 0.1 |
| Zinc lactate | 0.1 |
| Germall Plus | 0.2 |
| Ethanol | 58 |
| Ispropanol | 2.0 |
| Silicone (Dimethicone) | 0.2 |
| Incroquat Behentyl TMS | 0.7 |
| Polawax A31 | 0.3 |
| Glycerin | 1.0 |
| Cetyl ether (PPG10) | 0.5 |
| CHG | 0.05 |
| BZK | 0.02 |
| Farnesol | 0.3 |

Alcohol Zinc Gel for Use Under Latex Glove

| Ingredients | % by weight |
|---|---|
| Ucare JR30-M | 0.8 |
| Methocel K100 | 0.3 |
| Water | 27.13 |
| Zinc gluconate | 0.6 |
| Zinc acetate | 0.2 |
| Zinc lactate | 0.2 |
| Germall Plus | 0.2 |
| Zinc stearate | 1.5 |
| Zinc oxide | 1.0 |
| Glucate DO | 5.0 |
| Ethanol | 55.0 |
| Ispropanol | 3.0 |
| Silicone (Dimethicone) | 0.5 |
| Incroquat Behenyl TMS | 1.0 |
| Polawax A31 | 0.5 |
| Glycerin | 2.0 |
| Cetyl ether (PPG10) | 1.0 |
| CHG | 0.05 |
| BZK | 0.02 |
| Farnesol | 0.3 |
| Vitamin E | 0.2 |

Triple Zinc Anti-Itch Lotion with EO and FF Ingredients

| Ingredients | (% by wt) |
|---|---|
| Incroquat Behenyl TMS | 0.8 |
| Polawax NF | 0.8 |
| Petroleum Jelly | 3.0 |
| Crothix | 1.0 |
| Crodomol MM | 1.0 |
| Cromerol | 1.0 |
| Propylene glycol | 2.0 |
| Glycerin | 8.0 |
| Water | 77.4 |
| Ucare JR30 | 0.2 |
| Germall+ | 0.2 |
| Zinc gluconate | 0.3 |
| Zinc acetate | 0.1 |
| Zinc lactate | 0.1 |
| Zinc stearate | 3.0 |
| Zinc oxide | 0.5 |
| Farnesol | 0.3 |
| Lemon oil | 0.3 |

Anti-Irritant Disinfectant Soap with EO and FF Ingredients

| Ingredients | % By weight |
|---|---|
| Polyox WSR 205 | 0.1 |
| UCare Jr30-M | 0.2 |
| Germall Plus | 0.2 |
| Water | 86.93 |
| Pluronic F87 | 2.0 |
| Cocoamidopropylbetaine | 1.0 |
| Mirapol A-15 | 1.0 |
| Propylene glycol | 2.0 |
| Polyquaternium-47(Merquat 3330) | 3.0 |
| Glycerin | 2.0 |
| CHG | 0.05 |
| BZK | 0.12 |
| Triclosan | 0.3 |
| Farnesol | 0.3 |
| Lemon oil | 0.3 |
| Zinc acetate | 0.1 |
| Zinc lactate | 0.1 |
| Zinc gluconate | 0.3 |

Various publications and have been referenced herein, the contents of which are hereby incorporated by reference in their entireties.

What is claimed is:

1. An anti-irritant composition comprising:

(a) two or more water-soluble, organic salts of zinc selected from the group consisting of zinc acetate, zinc butyrate, zinc citrate, zinc gluconate, zinc glycerate, zinc glycolate, zinc formate, zinc lactate, zinc picolinate, zinc proprionate, zinc tartrate and zinc undecylenate, wherein said water-soluble, organic salts of zinc are present in said anti-irritant composition at concentrations between 0.1% and 2% (weight/weight), (b) [one or more antimicrobial compounds selected from the group consisting of] chlorhexidine gluconate[,] *and* benzalkonium chloride, [and combinations thereof wherein] each of [the one or more antimicrobial compounds] *which* are present at a concentration of between 0.05%-4% (weight/weight), (c) 0.05%-[4] *3*% (weight/weight) [incroquat] *Incroquat Behenyl TMS*, (d) water, (e) 60%-95% ethanol, and (f) one or more agent selected from the group consisting of a gelling agent, a thickening agent, a hydrophilic or hydrophobic polymer, an emulsifying agent, and an emollient, wherein the [composition exhibits] *chlorhexidine gluconate, benzalkonium chloride and Incroquat Behenyl TMS are present in amounts which exhibit* a synergistic preservative effect against bacteria.

2. The anti-irritant composition of claim 1, wherein the concentration of water is between 10% and [80] *32.25*% (weight/weight).

3. The anti-irritant composition of claim 1, wherein the concentration of the emollient is between 0.3% and 10.0% (weight/weight).

4. The anti-irritant composition of claim 1, wherein the emollient is selected from the group consisting of PEG 20 almond glycerides, Probutyl DB-10, Glucam P-20, Glucam E-10, Glucam P-10, Glucam E-20, Glucam P-20 distearate, glycerin, propylene glycol, cetyl acetate, acetylated lanolin alcohol, cetyl ether, myristyril ether, hydroxylated milk glycerides, polyquaternium compounds, copolymers of dimethyl dialyl ammonium chloride and acrylic acid, dipropylene glycol methyl ethers, polypropylene glycol ethers, silicon polymers, petrolatum, mineral oil, lanolin, olive oil, cocoa butter, shea butter, cetyl lactate, lauryl lactate, isopropyl lanolate, 2-ethylhexyl salicylate, cetyl myristate, oleyl myristate, oleyl stearate, oleyl oleate, hexyl laurate, isohexyl laurate, and combinations thereof.

5. The anti-irritant composition of claim 1, wherein the concentration of the gelling or thickening agent is between 0.05% and 10.0% (weight/weight).

6. The anti-irritant composition of claim 5, wherein the gelling and/or thickening agent is selected from the group consisting of cationic hydroxy ethyl cellulose, crothix, crodomol, zinc stearate, behenyl alcohol, and combinations thereof.

7. The anti-irritant composition of claim 1 which further comprises between 0.1% and 1.0% (weight/weight) silicone polymer.

8. The anti-irritant composition of claim 7, wherein the silicone polymer is selected from a group consisting of polydimethylsiloxane polymer, dimethiconol fluid in dimethicone, cyclomethicone and dimethicone copolyl, silicone glycol, and combinations thereof.

9. The anti-irritant composition of claim 1, further comprising an antimicrobial compound selected from the group consisting of iodopropynylbutyl carbamate, phenoxyethanol, polymyxin B, neomycin, triclosan, parachlorometaxylene, octoxyglycerin, and combinations thereof.

10. The anti-irritant composition of claim 1 which further comprises a stabilizing agent at a concentration of between 0.1% and 1.0% (weight/weight).

11. The anti-irritant composition of claim 10, wherein the stabilizing agent is selected from the group consisting of antioxidants, surfactants, and combinations thereof.

12. The anti-irritant composition of claim 11, wherein the surfactant is selected from the group consisting of incromide or a silicone-based surfactant.

13. The anti-irritant composition of claim 11, wherein the antioxidant is selected from the group consisting of vitamin C, vitamin E, and combinations thereof.

14. The anti-irritant composition of claim 1, which further comprises one or more natural or synthetic chemicals selected from the group consisting of an almond oil, ylang-ylang oil, neroli oil, sandalwood oil, frankincense oil, peppermint oil, lavender oil, jasmine absolute, geranium oil bourbon, spearmint oil, clove oil, lemongrass oil, cedarwood oil, balsam oils, tangerine oil, 1-citronellol, α-amylcinnamaldehyde, lyral, geraniol, hydroxycitronellal, isoeugenol, eugenol, eucalyptus oil, eucalyptol, lemon oil, linalool, citral and combinations thereof.

15. The anti-irritant composition of claim 1, which further comprises farnesol.

[16. An anti-irritant composition comprising:

(a) two or more water-soluble, organic salts of zinc selected from the group consisting of zinc acetate, zinc butyrate, zinc citrate, zinc gluconate, zinc glycerate, zinc glycolate, zinc formate, zinc lactate, zinc picolinate, zinc proprionate, zinc tartrate and zinc undecylenate, wherein said water-soluble, organic salts of zinc are present in said anti-irritant composition at concentrations between 0.1% and 2% (weight/weight), (b) one or more anti-microbial agents, wherein each of the one or more antimicrobial compounds are present at a concentration of between 0.05% and 4% (weight/weight), (c) 0.05%-4% (weight/weight) incroquat, (d) water, (e) ethanol, and (f) one or more agents selected from the group consisting of a gelling agent, a thickening agent, a hydrophilic or hydrophobic polymer, an emulsifying agent, and an emollient.]

* * * * *